US007256218B2

(12) United States Patent
Jacobus et al.

(10) Patent No.: US 7,256,218 B2
(45) Date of Patent: Aug. 14, 2007

(54) BIGUANIDE AND DIHYDROTRIAZINE DERIVATIVES

(75) Inventors: David P. Jacobus, Princeton, NJ (US); Guy A. Schiehser, Washington Crossing, PA (US); Hong-Ming Shieh, Newtown, PA (US); Norman P. Jensen, San Rafael, CA (US); Jacek Terpinski, North Brunswick, NJ (US)

(73) Assignee: Jacobus Pharmaceutical Company, Inc., Princeton, NJ (US)

( * ) Notice: Subject to any disclaimer, the term of this patent is extended or adjusted under 35 U.S.C. 154(b) by 300 days.

(21) Appl. No.: 10/716,283

(22) Filed: Nov. 18, 2003

(65) Prior Publication Data

US 2004/0116428 A1 Jun. 17, 2004

Related U.S. Application Data

(60) Provisional application No. 60/428,306, filed on Nov. 22, 2002.

(51) Int. Cl.

| C07C 279/26 | (2006.01) |
| A61K 31/155 | (2006.01) |
| A61P 33/02 | (2006.01) |
| A61P 33/08 | (2006.01) |
| C07D 317/14 | (2006.01) |
| C07D 319/14 | (2006.01) |
| A61K 31/357 | (2006.01) |
| A61K 31/36 | (2006.01) |

(52) U.S. Cl. ............... 514/633; 514/635; 514/452; 514/464; 556/233; 556/234; 556/235; 549/365; 549/462

(58) Field of Classification Search ............... 546/234; 564/233, 235, 234; 514/633, 635, 452, 464; 549/365, 462

See application file for complete search history.

(56) References Cited

U.S. PATENT DOCUMENTS

| 3,723,429 | A | 3/1973 | Mamalis et al. | ......... 260/249.9 |
| 4,179,562 | A | 12/1979 | Ponsford | ............ 544/298 |
| 4,232,022 | A | 11/1980 | Ponsford | ............ 424/251 |
| 5,300,503 | A | 4/1994 | Peake et al. | ............ 514/245 |
| 5,322,858 | A | 6/1994 | Canfield et al. | ............ 514/635 |
| 5,538,812 | A | 7/1996 | Lee et al. | ............ 429/192 |

FOREIGN PATENT DOCUMENTS

GB   1 250 531   10/1971

OTHER PUBLICATIONS

Snyder et al., J. Med. Liban 48(4): 208-214, 2000.*
Bergeron, R.J., et al., "Mild oxidation of alkyl halides," *J. Org. Chem.*, 1979, 44(11), 1835-1839.
Carey, F.A., et al., Advanced Organic Chemistry, Part B: Reactions and Synthesis, 3rd Ed., *Plenum Press*, New York, 1990, 588-591.
Crowther, A.F., "Synthetic antimalarials. Part XXIX. The preparation of some $N^1$-aryl-$N^2$-alkyl-$N^5$-alkyl- and -dialkyl-diguanides," *J. Chem. Soc.*, 1948, 1636-1645.
Curd, F.H.S., et al., "Synthetic antimalarials. Part XXVIII. An alternative route to $N^1$-aryl-$N^5$-alkyldiguanides," *J. Chem. Soc.*, 1948, 1630-1635.
Davidson, J.S., "A preparation of *N*-alkyl-*N*-cyano-*S*-methylisothioureas," *Chemistry and Industry*, Nov. 27, 1965, 1977-1978.
Gennaro, A.R. (Ed.), Remington's Pharmaceutical Sciences, 17th Ed., *Mack Publishing Co.*, Easton, PA, 1985.
Greene, T.W., et al., Protective Groups in Organic Synthesis, 2nd Ed., *John Wiley & Sons, Inc.*, 1991, 117-118.
Jensen, N.P., et al., "Phenoxypropoxybiguanides, prodrugs of DHFR—inhibiting diaminotriazine antimalarials," *J. Med. Chem.*, 2001, 44, 3925-3931.
Knight, D.J., et al., "The antimalarial activity of N-benzyloxydihydrotriazines," *Annals. of Tropical Med. & Parasitol.*, 1980, 74(4), 393-404.
Knight, D.J., et al., "The antimalarial activity of N-benzyloxydihydrotriazines," *Annals of Trop. Med. & Parasitol.*, 1982, 76(1), 9-14.
Larock, R.C., Comprehensive Organic Transformation,: *VCH Publishers*, New York, 1989, 353-363.
Onori, E., et al., "Recent acquisitions on chemotherapy and chemoprophylaxis of malaria," *Ann. 1st Super Sanita.*, 1989, 25(4), 659-673.
The PCT International Search Report dated May 6, 2004 (PCT/US03/37511).

* cited by examiner

*Primary Examiner*—Venkataraman Balasubramanian
(74) *Attorney, Agent, or Firm*—Woodcock Washburn LLP

(57) ABSTRACT

Biguanide and dihydrotriazine derivatives, preferably substituted asymmetrical imidodicarbonimidic diamides derived from hydroxylamines, and compositions containing biguanide and dihydrotriazine derivatives are disclosed. In addition, methods of using the biguanide and dihydrotriazine derivatives, inter alia, as antimicrobial agents and methods of using the dihydrotriazine derivatives in biological assays are disclosed. Methods of making the biguanide and dihydrotriazine derivatives are also disclosed.

91 Claims, No Drawings

BIGUANIDE AND DIHYDROTRIAZINE DERIVATIVES

CROSS REFERENCE TO RELATED APPLICATIONS

This application claims the benefit of application Ser. No. 60/428,306, filed Nov. 22, 2002, the disclosure of which is incorporated by reference in its entirety.

FIELD OF THE INVENTION

The present invention generally relates to biguanide and dihydrotriazine derivatives. More specifically, the present invention relates to biguanide and dihydrotriazine derivatives, compositions containing biguanide and dihydrotriazine derivatives, methods of using the biguanide and dihydrotriazine derivatives, inter alia, as antimicrobial agents, and methods of making the biguanide and dihydrotriazine derivatives.

BACKGROUND OF THE INVENTION

Certain dihydrotriazine derivatives have been explored as antimalarial compositions (Onori et al., *Ann. 1st Super Sanita.*, 1989, 25:659-74). However, they are poorly absorbed and have been shown to be less effective in eliciting cures when administered orally, as compared to injection, to malaria-infected Aotus monkeys. These triazine derivatives must be administered by injection to observe activity comparable to or exceeding other known antimalarial drugs and are poorly tolerated when given by the oral route. (Knight et al., *I. Ann. Tropical Med. Parasitol.*, 1980 74:393-404; Knight et al, *IV. Ann. Trop. Med. Parasitol.* 1982 76:9-14; U.S. Pat. No. 4,232,022; and U.S. Pat. No. 4,179,562).

Certain other dihydrotriazine derivatives have been explored as antimicrobial or antimalarial compositions. (U.S. Pat. No. 3,723,429)

U.S. Pat. No. 5,322,858 discloses biguanide derivatives, including $N^1,N^5$-substituted asymmetrical imidodicarbonimidic diamides, having antimicrobial and antiparasitic activity of various kinds, including antimalarial and antituberculosis activity, and discloses that such compounds provide elevated levels of bioavailability due to their ready absorption when taken orally. While the imidodicarbonimidic diamides exhibited inherent biological activities in claimed therapeutic applications, significant activities of the claimed compounds may arise by virtue of their conversions, in vivo, to the corresponding dihydrotriazine metabolites.

More recently, Jensen, et al., *J. Med. Chem.* 2001, 44, 3925-3931 reported a series of dihydrofolate reductase inhibitors that were effective as antimalarial agents, and unlike earlier antimalarial agents, were not cross-resistant with their previous counterparts.

In view of the importance of pharmaceutical compounds with these types of biological activity in the treatment of malaria, and other microbial and parasitic-type diseases and afflictions, compounds with enhanced pharmaceutical properties, and their methods of manufacture, are needed. Such improvements may include, for example, one or more of the following: enhanced biological activity, decreased toxicity, improved stability, better patient drug tolerance, increased solubility, in-use cost effectiveness, improved bioavailability, ease of drug administration, simplicity of manufacture, use of more environmentally friendly reagents, reduced environmental impact of co-generated by-products and their related waste disposal issues, and the like.

The compounds, processes for their manufacture, methods of use, and compositions of the present invention are directed to these, as well as other, important needs.

SUMMARY OF THE INVENTION

The present invention is generally directed to biguanide and dihydrotriazine derivatives, preferably substituted asymmetrical imidodicarbonimidic diamides derived from hydroxylamines, and compositions containing biguanide and dihydrotriazine derivatives. In addition, the present invention is generally directed to methods of using the biguanide and dihydrotriazine derivatives, inter alia, as antimicrobial agents and methods of using the dihydrotriazine derivatives in biological assays. The present invention is generally directed to methods of making the biguanide and dihydrotriazine derivatives.

In one embodiment, the invention is directed to compounds of the formula I or formula XIII or a pharmaceutically acceptable salt thereof, and all equivalent tautomeric forms thereof:

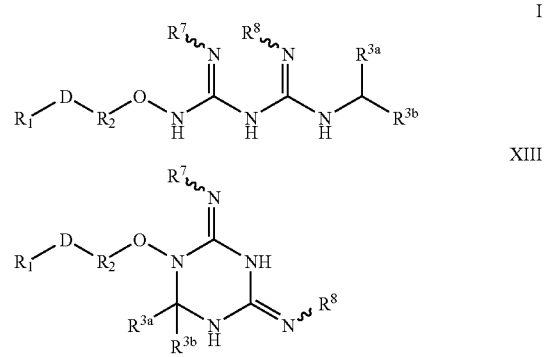

wherein:

$R^1$ is $R^x$, substituted aryl, substituted alkyl, substituted fused cycloalkylaryl, substituted aralkyl, substituted cycloalkylalkyl, substituted heteroaryl, or substituted heteroarylalkyl, wherein the latter seven groups are substituted with at least one substituent selected from the group consisting of —CN, —OCF$_3$, haloalkoxy, —SR$^4$, —OCF$_3$, —SCF$_3$, haloalkylthio, —NR$^5$R$^6$, —SO$_2$R$^4$, —SO$_2$NR$^5$R$^{6a}$, heteroaryl, heterocyclyl or $R^{10}O$—(CH$_2$CH$_2$O)$_j$—, or combinations thereof;

$R^x$ is substituted or unsubstituted:

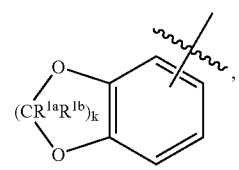

wherein each $R^{1a}$ and $R^{1b}$ are independently H, alkyl or fluoro;

$R^2$ is branched or straight chain lower alkylidene, or lower alkylene;

$R^{3a}$ and $R^{3b}$ are each independently hydrogen, lower alkyl, lower alkenyl, lower alkynyl, or taken together form a cycloalkyl or spiroalkyl group;

each $R^4$ is independently hydrogen, lower alkyl, substituted lower alkyl, lower alkenyl, substituted lower alkenyl, lower alkynyl, substituted lower alkynyl, aryl, substituted aryl, haloaryl, acyl, or heterocyclyl;

each $R^5$ is independently hydrogen, alkyl, substituted lower alkyl, lower alkenyl, substituted lower alkenyl, lower alkynyl, substituted lower alkynyl, alkyl substituted aryl, or acyl;

each $R^6$ is independently hydrogen, alkyl, substituted lower alkyl, lower alkenyl, substituted lower alkenyl, lower alkynyl, substituted lower alkynyl, alkyl substituted aryl, acyl, —$SO_2R^5$, or $SO_2NR^5R^5$; or $R^5$ and $R^6$ taken together with the atom to which they are attached form a heterocycle;

each $R^{6a}$ is independently hydrogen, alkyl, substituted lower alkyl, lower alkenyl, substituted lower alkenyl, lower alkynyl, substituted lower alkynyl, alkyl substituted aryl, acyl; or $R^5$ and $R^{6a}$ taken together with the atom to which they are attached form a heterocycle;

$R^7$ and $R^8$ are each, independently, hydrogen, alkyl, or acyl;

D is lower alkylidene, lower alkylene, —O—, —S—, or —N($R^9$)—;

$R^9$ is hydrogen, alkyl, substituted lower alkyl, lower alkenyl, substituted lower alkenyl, lower alkynyl, substituted lower alkynyl, alkyl-substituted aryl, or acyl;

$R^{10}$ is alkyl or haloalkyl;

j is an integer from 1 to 20; and k is an integer from 1 to 4;

provided that, in a compound of formula XIII, when $R^{3a}$ and $R^{3b}$ are each independently H, lower alkyl, or taken together form a cycloalkyl or spiroalkyl group and $R^7$ and $R^8$ are each hydrogen, then $R^1$ is $R^x$ or is substituted with at least one substituent from the group consisting of —$OCF_3$, haloalkoxy, and $R^{10}O$—$(CH_2CH_2O)_j$—.

In another embodiment, the invention is directed to compositions, comprising:

at least one compound of formula I or formula XIII; and at least one pharmaceutically acceptable carrier.

In yet another embodiment, the invention is directed to process for preparing antimicrobial compounds, comprising the steps of:

contacting a compound of formula II:

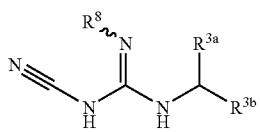

II with a compound of formula III:

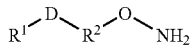

III for a time and under conditions sufficient to provide a compound of formula I:

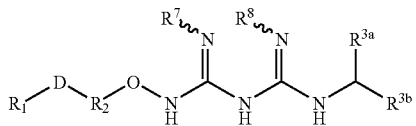

I wherein:

$R^1$ is $R^x$, substituted aryl, substituted alkyl, substituted fused cycloalkylaryl, substituted aralkyl, substituted cycloalkylarylalkyl, substituted heteroaryl, or substituted heteroarylalkyl, wherein the latter seven groups are substituted with at least one substituent selected from the group consisting of —CN, —$OCF_3$, haloalkoxy, —$SR^4$, —$OCF_3$, —$SCF_3$, haloalkylthio, —$NR^5R^6$, —$SO_2R^4$, —$SO_2NR^5R^{6a}$, heteroaryl, heterocyclyl or $R^{10}O$—$(CH_2CH_2O)_j$—, or combinations thereof;

$R^x$ is substituted or unsubstituted:

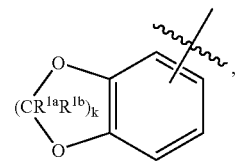

wherein each $R^{1a}$ and $R^{1b}$ are independently H, alkyl or fluoro;

$R^2$ is branched or straight chain lower alkylidene, or lower alkylene;

$R^{3a}$ and $R^{3b}$ are each independently hydrogen, lower alkyl, lower alkenyl, lower alkynyl, or taken together form a cycloalkyl or spiroalkyl group;

each $R^4$ is independently hydrogen, lower alkyl, substituted lower alkyl, lower alkenyl, substituted lower alkenyl, lower alkynyl, substituted lower alkynyl, aryl, substituted aryl, haloaryl, acyl, or heterocyclyl;

each $R^5$ is independently hydrogen, alkyl, substituted lower alkyl, lower alkenyl, substituted lower alkenyl, lower alkynyl, substituted lower alkynyl, alkyl substituted aryl, or acyl;

each $R^6$ is independently hydrogen, alkyl, substituted lower alkyl, lower alkenyl, substituted lower alkenyl, lower alkynyl, substituted lower alkynyl, alkyl substituted aryl, acyl, —$SO_2R^5$, or $SO_2NR^5R^5$; or $R^5$ and $R^6$ taken together with the atom to which they are attached form a heterocycle;

each $R^{6a}$ is independently hydrogen, alkyl, substituted lower alkyl, lower alkenyl, substituted lower alkenyl, lower alkynyl, substituted lower alkynyl, alkyl substituted aryl, acyl; or $R^5$ and $R^{6a}$ taken together with the atom to which they are attached form a heterocycle;

$R^7$ and $R^8$ are each, independently, hydrogen, alkyl, or acyl;

D is lower alkylidene, lower alkylene, —O—, —S—, or —N($R^9$)—;

$R^9$ is hydrogen, alkyl, substituted lower alkyl, lower alkenyl, substituted lower alkenyl, lower alkynyl, substituted lower alkynyl, alkyl-substituted aryl, or acyl;

$R^{10}$ is alkyl or haloalkyl;

j is an integer from 1 to 20; and k is an integer from 1 to 4;

or a pharmaceutical acceptable salt thereof.

In yet other embodiments, the invention is directed to methods for reducing in a patient the level of infection caused by an organism selected from the group consisting of *Plasmodium* sp., *Mycobacterium* sp., *Toxoplasma gondii*, and *Pneumocystis carinii*, comprising the step of:

administering to said patient in need thereof an effective amount of at least one compound of formula I or formula XIII.

In yet further embodiments, the invention is directed to methods for protecting a patient susceptible to infection caused by exposure to an organism selected from the group consisting of *Plasmodium* sp., *Mycobacterium* sp., *Toxoplasma gondii*, and *Pneumocystis carinii*, comprising the step of:

administering to said patient in need thereof an effective amount of at least one compound of formula I or formula XIII.

In other embodiments, the invention is directed to methods of evaluating the in vivo biological activity of a compound of formula I, comprising the step of:

assaying in vitro for the biological activity of the product of the oxidative cyclization of the compound of formula I.

DETAILED DESCRIPTION OF THE INVENTION

The present invention is generally directed to biguanide and dihydrotriazine derivatives, preferably substituted asymmetrical imidodicarbonimidic diamides derived from hydroxylamines, and compositions containing biguanide and dihydrotriazine derivatives. In addition, the present invention is generally directed to methods of using the biguanide and dihydrotriazine derivatives, inter alia, as antimicrobial agents and methods of using the dihydrotriazine derivatives in biological assays. The present invention is generally directed to methods of making the biguanide and dihydrotriazine derivatives.

As employed above and throughout the disclosure, the following terms, unless otherwise indicated, shall be understood to have the following meanings.

As used herein, the term "contacting" refers to the bringing together of compounds to within distances that allow for intermolecular interactions and chemical transformations accompanying such interactions. Often, contacting compounds are in solution phase.

As used herein, "alkyl" refers to a saturated straight, branched, cyclic, or multicyclic hydrocarbon having from 1 to about 20 carbon atoms (and all combinations and subcombinations of ranges and specific numbers of carbon atoms therein). The term "lower alkyl" herein refers to those alkyl groups having from about 1 to about 10 carbon atoms, these being preferred. Alkyl groups include, but are not limited to, methyl, ethyl, n-propyl, isopropyl, cyclopropyl, n-butyl, isobutyl, t-butyl, cyclobutyl, n-pentyl, cyclopentyl, isopentyl, neopentyl, n-hexyl, isohexyl, cyclohexyl, cycloheptyl, cyclooctyl, decahydronaphthalenyl, adamantyl, 3-methylpentyl, 2,2-dimethylbutyl, and 2,3-dimethylbutyl. Alkyl groups can be substituted or unsubstituted. In certain embodiments, preferred alkyl groups include isopropyl and cyclopropyl.

As used herein, "haloalkyl" means an alkyl group substituted with one or more halo groups selected from —F or —Cl.

As used herein, "alkoxy" means an alkyl-O— moiety, wherein "alkyl" as defined above.

As used herein, "haloalkoxy" means an alkoxy group substituted with one or more halo groups selected from —F and —Cl.

As used herein, "cycloalkyl" refers to an alkyl group having one or more rings in their structures. Multi-ring structures may be bridged or fused ring structures. The term "lower cycloalkyl" herein refers to those cycloalkyl groups having from about 3 to about 10 carbon atoms.

As used herein, "alkylidene" refers to a bivalent aliphatic radical derived from univalent aliphatic or cycloaliphatic hydrocarbon radicals whose names end in "yl" by removal of one of the hydrogen atoms from the carbon atom with the free valence, the radical having from about 1 to about 20 carbon atoms (and all combinations and subcombinations of ranges and specific numbers of carbon atoms therein). "Lower alkylidene" refers to those divalent aliphatic and cycloaliphatic groups with from about 1 to about 10 carbon atoms. Alkylidene groups include, but are not limited to, methylidene, ethylidene, n-propylidene, isopropylidene, cyclopropylidene, n-butylidene, isobutylidene, t-butylidene, 2-butenylidene, 2-butynylidene, n-pentylidene, cyclopentylidene, isopentylidene, neopentylidene, n-hexylidene, isohexylidene, cyclohexylidene, cyclooctylidene, adamantylidene, 3-methylidene pentylidene, 2,2-dimethylidene butylidene, and 2,3-dimethylbutylidene. Alkylidene groups can be substituted or unsubstituted.

As used herein, "alkylene" refers to a bivalent alkyl radical having the general formula $-(CH_2)_n-$, where n is 1 to 20. Non-limiting examples include methylene, trimethylene, pentamethylene, and hexamethylene. Alkylene groups may also contain one or more double or triple bonds within the backbone of the $-(CH_2)_n-$ moiety, provided that $n \geq 2$ and that the resultant compound is stable. Non-limiting examples include $-CH_2-C \equiv C-CH_2-$ and $CH_2-CH=CH-CH_2-$. Alkylene groups can be substituted or unsubstituted. The term "lower alkylene" herein refers to those alkylene groups having from about 1 to about 10 carbon atoms.

As used herein, "alkenyl" refers to an alkyl group having one or more double bonds. The term "lower alkenyl" herein refers to those alkenyl groups having from about 2 to about 10 carbon atoms.

As used herein, "alkynyl" refers to an alkyl group having one or more triple bonds. The term "lower alkynyl" herein refers to those alkynyl groups having from about 2 to about 10 carbon atoms.

As used herein, "aryl" refers to a mono-, di-, tri-, or other multicyclic aromatic ring system having from about 5 to about 30 carbon atoms (and all combinations and subcombinations of ranges and specific numbers of carbon atoms therein), with from about 6 to about 14 carbons being preferred. Non-limiting examples include phenyl, naphthyl, anthracenyl, and phenanthrenyl. Aryl groups can be substituted or unsubstituted.

As used herein, "haloaryl" refers to means an aryl group substituted with one or more halo groups selected from —F, —Cl, and —Br.

As used herein, "aralkyl" or "arylalkyl" refers to aryl-substituted alkyl radicals having from about 6 to about 50 carbon atoms (and all combinations and subcombinations of ranges and specific numbers of carbon atoms therein), with from about 6 to about 20 carbon atoms being preferred. Non-limiting examples include, for example, benzyl, phenylethyl, 3-phenylprop-1-yl, tetrahydronaphthalenyl, 3-phenylprop-2-yl, and 4-naphthylhex-1-yl. Aralkyl groups can be substituted or unsubstituted. Substitution may occur on the aryl ring carbons or alkyl carbons of the aralkyl.

As used herein, "heteroaryl" refers to a mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrrolyl, furyl, pyridyl, 1,2,4-thiadiazolyl, pyrimidinyl, isothiazolyl, thiazolyl, triazolyl, imidazolyl, tetrazolyl, pyrazinyl, quinolyl, isoquinolyl, thiophenyl, benzothienyl, isobenzofuryl, pyrazolyl, indolyl, purinyl, carbazolyl, benzimidazolyl, oxazolyl, and isoxazolyl. Heteroaryl groups can be substituted or unsubstituted.

As used herein, "heteroarylalkyl" refers to heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl. Heteroarylalkyl groups can be substituted or unsubstituted. Substitution may occur on the heteroaryl ring carbons or alkyl carbons of the heteroarylalkyl.

As used herein, "fused cycloalkylaryl" refers to aryl radicals substituted at each of two adjacent ring carbon atoms with one terminus of an "alkylene" diradical, so as to form a second moiety whose cycloalkyl ring is defined by the two adjacent aryl ring carbons and the carbons of the "alkylene" diradical. "Fused cycloalkylaryl" groups can have from about 8 to about 40 carbon atoms (and all combinations and subcombinations of ranges and specific numbers of carbon atoms therein), with from about 9 to about 20 carbons being preferred. Non-limiting examples include tetrahydronaphthalenyl, hexahydro-benzocycloocte-nyl, indanyl, and 2, 3, 3a, 4, 5, 9b-hexahydro-1H-cyclopenta[a]naphthalen-8-yl. "Fused cycloalkylaryl" groups may be substituted or unsubstituted. Substitution may occur on the aryl ring carbons or cycloalkyl ring carbons of the fused cycloalkylaryl.

As used herein, "cycloalkylarylalkyl" or "cycloalkylaralkyl" refers to cycloalkyl-substituted aralkyl radicals having from about 10 to about 50 carbon atoms (and all combinations and subcombinations of ranges and specific numbers of carbon atoms therein), with from about 12 to about 25 carbon atoms being preferred. Non-limiting examples include, for example, para-cyclohexylbenzyl, 3-cyclopropylphenylethyl, and 3-[4-cyclopentylphenyl]-prop-1-yl. Cycloalkylarylalkyl groups can be substituted or unsubstituted. Substitution may occur on the aryl ring carbons or alkyl carbons of the aralkyl, or on the ring carbons of the cycloalkyl.

As used herein, "acyl" refers to an alkyl-C(=O)— or an aryl-C(=O)— group.

Typically, substituted chemical moieties include one or more substituents that replace hydrogen. Exemplary substituents include, for example, halo (e.g., —F, —Cl, —Br), (provided that when halo is —Br, the —Br is attached to an $sp^2$ carbon such as on a carbon of an alkenyl or a ring carbon of aryl or heteroaryl group), alkoxy, haloalkoxy, —$OCF_3$, alkylthio, monohaloalkylthio, polyhaloalkylthio, —$SCF_3$, alkyl, —$CF_3$, haloalkyl, lower alkyl, spiroalkyl, alkenyl, alkynyl, aralkyl, aryl, heteroaryl, heterocyclyl, hydroxyl (—OH), nitro (—$NO_2$), cyano (—CN), sulfonyl (—$SO_2R^4$), sulfamoyl (—$SO_2NR^5R^6$), —$SR^4$, amino (—$NH_2$, $NHR^5$, $NHR^6$, $N(R^5R^6)$ and the like.

As used herein, the term "spiroalkyl" refers to an alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro[4.7]dodecane. The spiroalkyl groups of this invention can be substituted or unsubstituted.

As used herein, "antimicrobial" refers to compounds having activity against pathogenic microorganisms such as bacteria, protozoa, yeasts, viruses, algae, fungi, or various other microscopic parasites including but not limited to those compounds having activity against the plasmodia of malaria (*P. berghei*), antimicrobial activity against mycobacteria including, but not limited to, *M. avium* intercellulare, *M. avium* complex, *M. tuberculosis, M. leprae* or *Toxoplasma gondii*, pneumocystis organisms such as *P. carinii*, or activity against nocardia infections.

As used herein, "side effect" refers to a consequence other than the one(s) for which an agent or measure is used, as the adverse effects produced by a drug, especially on a tissue or organ system other then the one sought to be benefited by its administration. In the case, for example, of antimalarial agents, the term "side effect" may preferably refer to such conditions as, for example, gastrointestinal, cardiac, hematological and central nervous system-related effects.

As used herein, "effective amount" refers to an amount of a compound as described herein that may be effective to inhibit, or treat the symptoms of particular disease, disorder, or side effect, or to prevent, inhibit, or diminish the onset the symptoms of particular disease, disorder, or side effect. Such diseases, disorders, and side effects include, but are not limited to, malaria, effects of malarial parasites, mycobacterium and pneumocystis infections, and dihydrofolate reductase-mediated, or modulated disorders.

As used herein, "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. Thus, the term "acid addition salt" refers to the corresponding salt derivative of a parent compound that has been prepared by the addition of an acid. The pharmaceutically acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Certain acidic or basic compounds of the present invention may exist as zwitterions. All forms of the compounds, including free acid, free base, and zwitterions, are contemplated to be within the scope of the present invention.

"Patient" refers to an animal, including a mammal, preferably a human.

Accordingly, the present invention is directed, in part, to compounds of the formula I or formula XIII or a pharmaceutically acceptable salt thereof, and all equivalent tautomeric forms thereof:

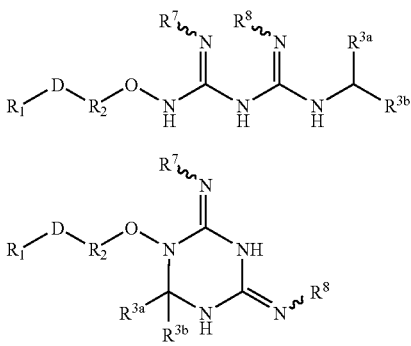

wherein:
R¹ is $R^x$, substituted aryl, substituted alkyl, substituted fused cycloalkylaryl, substituted aralkyl, substituted cycloalkylarylalkyl, substituted heteroaryl, or substituted heteroarylalkyl, wherein the latter seven groups are substituted with at least one substituent selected from the group consisting of —CN, —OCF₃, haloalkoxy, —SR⁴, —OCF₃, —SCF₃, haloalkylthio, —NR⁵R⁶, —SO₂R⁴, —SO₂NR⁵R⁶ᵃ, heteroaryl heterocyclyl or $R^{10}O$—$(CH_2CH_2O)_j$—, or combinations thereof;

$R^x$ is substituted or unsubstituted:

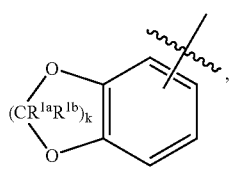

wherein each $R^{1a}$ and $R^{1b}$ are independently H, alkyl or fluoro;

R² is branched or straight chain lower alkylidene, or lower alkylene;

$R^{3a}$ and $R^{3b}$ are each independently hydrogen, lower alkyl, lower alkenyl, lower alkynyl, or taken together form a cycloalkyl or spiroalkyl group;

each R⁴ is independently hydrogen, lower alkyl, substituted lower alkyl, lower alkenyl, substituted lower alkenyl, lower alkynyl, substituted lower alkynyl, aryl, substituted aryl, haloaryl, acyl, or heterocyclyl;

each R⁵ is independently hydrogen, alkyl, substituted lower alkyl, lower alkenyl, substituted lower alkenyl, lower alkynyl, substituted lower alkynyl, alkyl substituted aryl, or acyl;

each R⁶ is independently hydrogen, alkyl, substituted lower alkyl, lower alkenyl, substituted lower alkenyl, lower alkynyl, substituted lower alkynyl, alkyl substituted aryl, acyl, —SO₂R⁵, or SO₂NR⁵R⁵; or R⁵ and R⁶ taken together with the atom to which they are attached form a heterocycle;

each $R^{6a}$ is independently hydrogen, alkyl, substituted lower alkyl, lower alkenyl, substituted lower alkenyl, lower alkynyl, substituted lower alkynyl, alkyl substituted aryl, acyl; or R⁵ and $R^{6a}$ taken together with the atom to which they are attached form a heterocycle;

R⁷ and R⁸ are each, independently, hydrogen, alkyl, or acyl;

D is lower alkylidene, lower alkylene, —O—, —S—, or —N(R⁹)—;

R⁹ is hydrogen, alkyl, substituted lower alkyl, lower alkenyl, substituted lower alkenyl, lower alkynyl, substituted lower alkynyl, alkyl-substituted aryl, or acyl;

R¹⁰ is alkyl or haloalkyl;

j is an integer from 1 to 20; and k is an integer from 1 to 4;

provided that, in a compound of formula XIII, when $R^{3a}$ and $R^{3b}$ are each independently H, lower alkyl, or taken together form a cycloalkyl or spiroalkyl group and R⁷ and R⁸ are each hydrogen, then R¹ is $R^x$ or is substituted with at least one substituent from the group consisting of —OCF₃, haloalkoxy, and $R^{10}O$—$(CH_2CH_2O)_j$—;

or a pharmaceutically acceptable salt thereof. Preferably, when R¹ is $R^x$, then $R^{1a}$ and $R^{1b}$ are each fluoro. More preferably, when $R^{1a}$ and $R^{1b}$ of $R^x$ are each fluoro, k is 1 or 2.

All forms of the compounds, including free acid, free base, and zwitterions, isomorphic crystalline forms, all chiral and racemic forms, hydrates, solvates, and acid salt hydrates, are contemplated to be within the scope of the present invention.

Compounds within the scope of the present invention have antimicrobial and antiparasitic activity of various kinds, including antimalarial activity. In some embodiments, they exhibit enhanced biological activity and/or decreased toxicity, especially when administered orally. Furthermore, in some embodiments, the compounds of the invention have shown a higher tolerated dose relative to the compounds disclosed in U.S. Pat. No. 5,322,858.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer.

The compounds of the present invention may exist in prodrug form. As used herein, "prodrug" is intended to include any covalently bonded carriers that release the active parent drug or whose form is converted, for example, to compounds of formula I or of formula XIII or of other formulas or compounds employed in the methods of the present invention, in vivo when such prodrug is administered to a patient. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs.

Prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like. Prodrugs also include, for example, compounds that cyclize or are metabolized in vivo to a form that is biologically active or enhanced in its biological activity, such as the oxidative metabolism of compounds of formula I to compounds of formula XIII.

When any variable occurs more than one time in any constituent or in any formula, its definition in each occurrence is independent of its definition at every other occurrence. Thus, for example, if an $R^1$ group is shown to be substituted with, for example, 1 to 5 of —CN, —OCF$_3$, haloalkoxy, —SCF$_3$, haloalkylthio, —SR$^4$, —NR$^5$R$^6$, —SO$_2$R$^4$, —SO$_2$NR$^5$R$^{6a}$, heteroaryl, or heterocyclyl, then the $R^1$ group may optionally be substituted with up to five of the above-mentioned substituents, and the substituent at each occurrence is selected independently from the above defined list of possible substituents. Combinations of substituents and/or variables are permissible only if such combinations result in stable compounds. It is further understood that, while certain substituents are minimally required, such as, for example in the $R^1$ moiety, the moiety may be further substituted with the same substituent(s), another substituent(s) from the group of required substituents, or other substituent(s) not from the group of required substituents.

In some embodiments of compounds of formula I or XIII, $R^1$ is substituted with at least one of —OCF$_3$, haloalkoxy, —SCF$_3$, haloalkylthio, or $R^{10}$O—(CH$_2$CH$_2$O)$_j$—.

In some embodiments of compounds of formula I or XIII, $R^1$ is $R^x$, wherein k is 1 or 2.

In some embodiments of compounds of formula I or XIII wherein $R^1$ is $R^x$, $R^{1a}$ and $R^{1b}$ are each independently H or F. In some preferred embodiments, $R^{1a}$ and $R^{1b}$ are each F.

In some embodiments of compounds of formula I or XIII, $R^x$ is substituted with one to four substituents selected, independently, from the group consisting of halo, —NO$_2$, —CN, —CF$_3$, —OCF$_3$, haloalkoxy, —SCF$_3$, haloalkylthio, haloalkyl, lower alkyl, spiroalkyl, aryl, alkoxy, —SR$^4$, —NR$^5$R$^6$, —SO$_2$R$^4$, —SO$^2$NR$^5$R$^{6a}$, heteroaryl, and heterocyclyl, and combinations thereof.

In some other embodiments of compounds of formula I or XIII, $R^x$, optionally substituted, is:

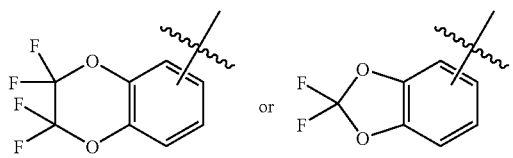

In some preferred embodiments of compounds of formula I or XIII, $R^x$ is:

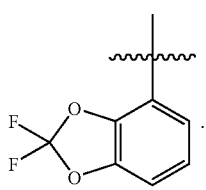

In other preferred embodiments of compounds of formula I or XIII, $R^x$ is:

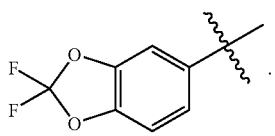

In certain preferred embodiments of compounds of formula I or XIII, $R^x$ is:

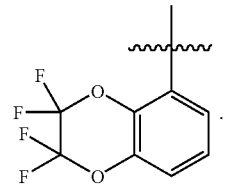

In yet other preferred embodiments of compounds of formula I or XIII, $R^x$ is:

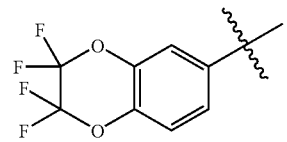

On certain other embodiments of formula I or XIII compounds, when $R^1$ is substituted aryl, substituted alkyl, substituted fused cycloalkylaryl, substituted aralkyl, substituted cycloalkylarylalkyl, substituted heteroaryl, or substituted heteroarylalkyl, it is further substituted with one to four substituents selected, independently, from the group consisting of halo, —NO$_2$, —CF$_3$, haloalkyl, lower alkyl, spiroalkyl, aryl, and alkoxy, and combinations thereof.

In some preferred embodiments of the compounds of formula I or XIII, $R^1$ substituted aryl, substituted fused cycloalkylaryl, substituted aralkyl, or substituted cycloalkylarylalkyl. More preferably, $R^1$ is substituted aryl. Even more preferably, $R^1$ is substituted phenyl, mono- or poly-substituted. More preferably still, when $R^1$ is mono-or poly-substituted phenyl, $R^{3a}$ and $R^{3b}$ are each independently lower alkyl, or taken together form a cyclopropyl or spiroalkyl group. Even more preferably, when $R^1$ is mono- or poly-substituted phenyl and $R^{3a}$ and $R^{3b}$ are each independently lower alkyl, or taken together form a cyclopropyl or spiroalkyl group, the substituted phenyl is substituted with at least one —OCF$_3$. In some still more preferred embodiments, $R^1$ is mono-substituted phenyl. Yet more preferred, $R^1$ is mono-substituted phenyl substituted with —OCF$_3$. Yet more preferred, when $R^1$ is mono-substituted phenyl substituted with —OCF$_3$, $R^{3a}$ and $R^{3b}$ are each independently methyl, or taken together form a cyclopropyl or spiroalkyl group. Even more preferred, when $R^1$ is mono-substituted phenyl substituted with —OCF$_3$ and $R^{3a}$ and $R^{3b}$ are each independently methyl, or taken together form a cyclopropyl or spiroalkyl group, $R^1$ is para-trifluoromethoxyphenyl and D is —O—.

In other preferred embodiments, when $R^1$ is para-trifluoromethoxyphenyl, $R^{3a}$ and $R^{3b}$ are each independently methyl, or taken together form a cyclopropyl or spiroalkyl group, and D is —O—, $R^7$ and $R^8$ are hydrogen. More preferred, when $R^1$ is para-trifluoromethoxyphenyl, $R^{3a}$ and $R^{3b}$ are each independently methyl, or taken together form a cyclopropyl or spiroalkyl group, D is —O—, and $R^7$ and $R^8$ are hydrogen, $R^2$ is —CH$_2$CH$_2$CH$_2$—. Even more preferred, when $R^1$ is para-trifluoromethoxyphenyl, $R^{3a}$ and $R^{3b}$ are each independently methyl, or taken together form a cyclopropyl or spiroalkyl group, D is —O—, $R^7$ and $R^8$ are hydrogen, and $R^2$ is —$CH_2CH_2CH_2$—, $R^{3a}$ and $R^{3b}$ are each methyl, or alternatively they form a cyclopropyl or spiroalkyl.

In other preferred embodiments when $R^1$ is mono- or polysubstituted phenyl; and wherein $R^{3a}$ and $R^{3b}$ are each independently lower alkyl, or taken together form a cycloalkyl or spiroalkyl group, the phenyl is substituted with at least one —$NR^5R^6$. Even more preferably, the para position of the mono- or polysubstituted phenyl is substituted with —$NR^5R^6$. In certain other preferred embodiments when $R^1$ is mono- or polysubstituted phenyl, the phenyl is substituted with at least one —$SR^4$. Even more preferably, the para position of the mono- or polysubstituted phenyl is substituted with —$SR^4$.

In yet other preferred embodiments, when $R^1$ is mono- or polysubstituted phenyl and the phenyl is substituted with at least one —$SR^4$, $R^4$ is substituted lower alkyl. More preferably, the substituted alkyl is substituted with at least one halo. Even more preferably, the halo is —F. More preferably still, the alkyl is —$CF_3$.

In some other more preferred embodiments when $R^1$ is mono- or polysubstituted phenyl, the phenyl is substituted with at least one —$SR^4$, and $R^4$ is —$CF_3$, $R^{3a}$ and $R^{3b}$ are each independently methyl, or taken together form a cyclopropyl or spiroalkyl group. More preferably, $R^{3a}$ and $R^{3b}$ are each independently methyl. More preferably still, when $R^1$ is mono- or polysubstituted phenyl and the phenyl is substituted with at least one —$SR^4$, $R^4$ is —$CF_3$, and $R^{3a}$ and $R^{3b}$ are each independently methyl, $R^2$ is —$CH_2CH_2CH_2$—. Even more preferably, when $R^1$ is mono- or polysubstituted phenyl, the phenyl is substituted with at least one —$SR^4$, $R^4$ is —$CF_3$, $R^{3a}$ and $R^{3b}$ are each independently methyl and $R^2$ is —$CH_2CH_2CH_2$—, D is —O—. Yet more preferably, when $R^1$ is mono- or polysubstituted phenyl and the phenyl is substituted with at least one —$SR^4$, $R^4$ is —$CF_3$, $R^{3a}$ and $R^{3b}$ are each independently methyl and $R^2$ is —$CH_2CH_2CH_2$—, $R^1$ is 4-(trifluoromethanethio)-phenyl, D is —O—, and $R^7$ and $R^8$ are each hydrogen.

In yet other preferred embodiments, when $R^1$ is mono- or polysubstituted phenyl and the phenyl is substituted with at least one —$SO_2R^4$, $R^4$ is substituted lower alkyl. More preferably, the substituted alkyl is substituted with at least one halo. Even more preferably, the halo is —F. More preferably still, the alkyl is —$CF_3$.

In some other more preferred embodiments when $R^1$ is mono- or polysubstituted phenyl, the phenyl is substituted with at least one —$SO_2R^4$, and $R^4$ is —$CF_3$, $R^{3a}$ and $R^{3b}$ are each independently methyl, or taken together form a cyclopropyl or spiroalkyl group. More preferably, $R^{3a}$ and $R^{3b}$ are each independently methyl. More preferably still, when $R^1$ is mono- or polysubstituted phenyl and the phenyl is substituted with at least one —$SO_2R^4$, $R^4$ is —$CF_3$, and $R^{3a}$ and $R^{3b}$ are each independently methyl, $R^2$ is —$CH_2CH_2CH_2$—. Even more preferably, when $R^1$ is mono- or polysubstituted phenyl, the phenyl is substituted with at least one —$SR^4$, $R^4$ is —$CF_3$, $R^{3a}$ and $R^{3b}$ are each independently methyl and $R^2$ is —$CH_2CH_2CH_2$—, D is —O—. Yet more preferably, when $R^1$ is mono- or polysubstituted phenyl, and the phenyl is substituted with at least one —$SO_2R^4$, $R^4$ is —$CF_3$, $R^{3a}$ and $R^{3b}$ are each independently methyl and $R^2$ is —$CH_2CH_2CH_2$—, $R^1$ is 4-(trifluoromethanesulfonyl)-phenyl, D is —O—, and $R^7$ and $R^8$ are each hydrogen.

In other preferred embodiments, when $R^1$ is mono- or polysubstituted phenyl and the phenyl is substituted with at least one —$NR^5R^6$, $R^6$ is $SO_2R^5$ or $SO_2NR^5R^{6a}$. More preferably, $R^6$ is $SO_2R^5$. More preferably still, when $R^6$ is $SO_2R^5$, $R^5$ is substituted low alkyl. Even more preferably, the substituted lower alkyl is substituted with at least one halo. Yet more preferably, the halo is —F. More preferably still, the alkyl is —$CF_3$.

In some other more preferred embodiments wherein $R^1$ is mono- or polysubstituted phenyl, the phenyl is substituted with at least one —$NR^5R^6$, $R^6$ is $SO_2R^5$, $R^5$ is substituted lower alkyl, and the substituted lower alkyl is —$CF_3$, $R^{3a}$ and $R^{3b}$ are each independently methyl, or taken together form a cyclopropyl or spiroalkyl group. More preferably, $R^{3a}$ and $R^{3b}$ are each independently methyl. More preferably still, when $R^1$ is mono- or poly-substituted phenyl, the phenyl is substituted with at least one —$NR^5R^6$, $R^6$ is $SO_2R^5$, $R^5$ is substituted lower alkyl, the substituted lower alkyl is —$CF_3$, and $R^{3a}$ and $R^{3b}$ are each independently methyl, $R^2$ is —$CH_2CH_2CH_2$—. Even more preferably, when $R^1$ is mono- or polysubstituted phenyl, the phenyl is substituted with at least one —$NR^5R^6$, $R^6$ is $SO_2R^5$, $R^5$ is substituted lower alkyl, the substituted lower alkyl is —$CF_3$, $R^{3a}$ and $R^{3b}$ are each independently methyl and $R^2$ is —$CH_2CH_2CH_2$—, $R^7$ and $R^8$ are each hydrogen D is —O—, and $R^1$ is 4-(trifluoromethanesulfonamido)-phenyl.

In some other still more preferred embodiments of the invention when $R^1$ is mono- or polysubstituted phenyl substituted with at least one —$OCF_3$, the phenyl is substituted with at least two —$OCF_3$. In other still more preferred embodiments the mono- or polysubstituted phenyl is substituted with at least one —$OCF_3$ and at least one halo. Multiple substitutions of each of halo and —$OCF_3$ are within the ambit of the invention, such as, 4,5-dihalo-2-trifluoromethoxyphenyl, and 5-halo-2,4-bis-trifluoromethoxyphenyl. Even more preferably, when the mono- or polysubstituted phenyl is substituted with at least one —$OCF_3$ and at least one halo, the halo is —Cl. In other even more preferred embodiments wherein $R^1$ is mono- or polysubstituted phenyl, the phenyl is substituted with two —$OCF_3$.

In some other more preferred embodiments wherein $R^1$ is mono- or polysubstituted phenyl and the phenyl is substituted with at least one —$OCF_3$ and at least one —Cl, $R^{3a}$ and $R^{3b}$ are each independently methyl, or taken together form a cyclopropyl or spiroalkyl group. More preferably, $R^{3a}$ and $R^{3b}$ are each independently methyl. More preferably still, when $R^1$ is mono- or polysubstituted phenyl and the phenyl is substituted with at least one —$OCF_3$ and at least one —Cl, and $R^{3a}$ and $R^{3b}$ are each independently methyl, $R^2$ is —$CH_2CH_2CH_2$—. Even more preferably, when $R^1$ is mono- or polysubstituted phenyl and the phenyl is substituted with at least one —$OCF_3$ and at least one —Cl, and $R^{3a}$ and $R^{3b}$ are each independently methyl, $R^2$ is —$CH_2CH_2CH_2$—, D is —O—.

In some other more preferred when $R^1$ is mono- or poly-substituted phenyl, the phenyl is substituted with at least two —$OCF_3$, $R^{3a}$ and $R^{3b}$ are each independently methyl, or taken together form a cyclopropyl or spiroalkyl group. More preferably, when $R^1$ is mono- or poly-substituted phenyl and the phenyl is substituted with at least two —$OCF_3$, $R^{3a}$ and $R^{3b}$ are each methyl. More preferably still, when $R^1$ is substituted phenyl, the phenyl is substituted with at least two —$OCF_3$, and $R^{3a}$ and $R^{3b}$ are each independently methyl, $R^2$ is —$CH_2CH_2CH_2$—. Even more preferably, when $R^1$ is substituted phenyl, the phenyl is substituted with at least two —$OCF_3$, $R^{3a}$ and $R^{3b}$ are each independently methyl and $R^2$ is —$CH_2CH_2CH_2$—, D is —O—.

In other still more preferred embodiments, when $R^1$ is mono- or poly-substituted phenyl, the phenyl is substituted with at least one —$OCF_3$, and $R^{3a}$ and $R^{3b}$ are each independently methyl, and $R^2$ is —CH$_2$CH$_2$CH$_2$—, D is —O—, $R^7$ and $R^8$ are each H and $R^1$ is 2,4-bis-trifluoromethoxyphenyl, 4-chloro-3-trifluoromethoxyphenyl, 4,5-dichloro-2-trifluoromethoxyphenyl, 2-chloro-4-trifluoromethoxyphenyl, or 4-chloro-2-trifluoromethoxyphenyl.

In other preferred embodiments of the compounds of formula I or XIII, $R^1$ is 2,4-bis-trifluoromethoxyphenyl, 4-chloro-3-trifluoromethoxyphenyl, 4,5-dichloro-2-trifluoromethoxyphenyl, 2-chloro-4-trifluoromethoxyphenyl, or 4-chloro-2-trifluoromethoxyphenyl. More preferably, when $R^1$ is 2,4-bis-trifluoromethoxyphenyl, 4-chloro-3-trifluoromethoxyphenyl, 4,5-dichloro-2-trifluoromethoxyphenyl, 2-chloro-4-trifluoromethoxyphenyl, or 4-chloro-2- trifluoromethoxyphenyl, $R^7$ and $R^8$ are each hydrogen and D is —O—.

In other preferred embodiments, $R^1$ is 4-(trifluoromethanethio)-phenyl, 4-(trifluoromethanesulfonyl)-phenyl or 4-(trifluoromethanesulfonamido)-phenyl. More preferably, when $R^1$ is 4-(trifluoromethanethio)-phenyl, 4-(trifluoromethanesulfonyl)-phenyl or 4-(trifluoromethanesulfonamido)-phenyl, $R^7$ and $R^8$ are each hydrogen and D is —O—.

In certain embodiments of the formula I or formula XIII compounds, $R^2$ may be substituted alkylene or substituted alkylidene. In other embodiments $R^2$ is alkylene, having the general formula —(CH$_2$)$_n$—, where n is one to ten. More preferably, n is one to five. Even more preferably, n is three to four. Most preferably, n is three. In other preferred embodiments, n is two to ten.

In certain embodiments of the formula I or formula XIII compounds, the $R^{3a}$ and $R^{3b}$ groups may be lower alkyl, lower alkenyl, or lower alkynyl, or taken together form a cycloalkyl or spiroalkyl group. Preferably, the $R^{3a}$ and $R^{3b}$ groups are each independently lower alkyl, or taken together form a cycloalkyl or spiroalkyl group. More preferably, the $R^{3a}$ and $R^{3b}$ groups are each independently methyl, or taken together form a cyclopropyl or spiroalkyl group.

In certain embodiments of the formula I or formula XIII compounds, the $R^7$ and $R^8$ groups may, each, independently, be hydrogen, alkyl, or acyl. Preferably they are each hydrogen. In other embodiments, no more that one of $R^7$ and $R^8$ is hydrogen.

In some preferred embodiments, $R^4$ is substituted lower alkyl. More preferably, the alkyl is substituted with halo. Even more preferably, the halo is fluoro. Yet more preferably, the substituted lower alkyl is —CF$_3$.

In some preferred embodiments, $R^4$ is hydrogen, lower alkyl, substituted lower alkyl, lower alkenyl, substituted lower alkenyl, aryl, substituted aryl, or haloaryl. In other preferred embodiments, $R^4$ is hydrogen, lower alkyl, substituted lower alkyl, aryl, substituted aryl, or haloaryl. In other preferred embodiments, $R^4$ is hydrogen, lower alkyl, substituted lower alkyl, aryl, or substituted aryl. In other preferred embodiments, $R^4$ is hydrogen, lower alkyl, or substituted lower alkyl. In yet other preferred embodiments, $R^4$ is lower alkyl, or substituted lower alkyl.

In some embodiments of the compounds of formula I or XIII, $R^1$ is substituted with —CN or —OCF$_3$. In other embodiments of the compounds of formula I or XIII, $R^1$ is substituted with —SCF$_3$, —SO$_2$CF$_3$, or —NHSO$_2$CF$_3$.

In some preferred embodiments, D is —O—, or —S—. More preferably, D is —O—.

In other preferred embodiments, D is lower alkylidene or lower alkylene. More preferably, D is lower alkylidene or lower alkylene.

In other preferred embodiments, j is an integer in the range of 1 to 10. More preferably, j is 1 to 6.

In other preferred embodiments, k is 1 or 2.

In other preferred embodiments, $R^1$ is para-trifluoromethoxyphenyl.

In some preferred embodiments, $R^6$ is hydrogen, alkyl, substituted lower alkyl, alkyl substituted aryl, $R^5$ and $R^6$ taken together with the atom to which they are attached form a heterocycle. In other preferred embodiments, $R^6$ and $R^{6a}$ are each independently hydrogen, alkyl, or substituted lower alkyl. In some preferred embodiments, $R^5$ and $R^6$ taken together with the atom to which they are attached form a heterocycle.

In some embodiments, $R^5$ is independently hydrogen, alkyl, substituted lower alkyl, or alkyl substituted aryl. In other preferred embodiments, $R^5$ is independently hydrogen, alkyl, or alkyl substituted aryl. In still other preferred embodiments, $R^5$ is independently hydrogen or alkyl.

In some preferred embodiments, $R^7$ and $R^8$ are each, independently, hydrogen or acyl. In other preferred embodiments, $R^7$ and $R^8$ are each hydrogen.

In any of these teachings, the compound of the invention may be either the compound of formula I, formula XIII, or a pharmaceutically acceptable salt thereof. Preferably, the compound is of formula I, more preferably a pharmaceutically acceptable salt of the compound of formula I.

Compounds of the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers Preferred compounds of the invention include:
1-(3-(4-trifluoromethoxyphenoxy)propyloxy)-5-isopropyl biguanide;
1-(3-(4-trifluoromethoxyphenoxy)propyloxy)-5-isopropyl biguanide hemisuccinate;
1-(3-(4-trifluoromethoxyphenoxy)propyloxy)-5-cyclopropyl biguanide;
1-(3-(4-trifluoromethoxyphenoxy)propyloxy)-5-cyclopropyl biguanide hydrochloride;
6,6-Dimethyl-1-[3-(4-trifluoromethoxy-phenoxy)-propoxy] [1,3,5]triazinane-2,4-diylidenediamine;
6,6-Dimethyl-1-[3-(4-trifluoromethoxy-phenoxy)-propoxy] [1,3,5]triazinane-2,4-diylidenediamine hydrochloride;
1-[3-(2-chloro-4-trifluoromethoxyphenoxy)propyloxy]-5-isopropyl biguanide;
1-[3-(2-chloro-4-trifluoromethoxyphenoxy)propyloxy]-5-isopropyl biguanide phosphate salt;
1-[3-(4-chloro-2-trifluoromethoxyphenoxy)propyloxy]-5-isopropyl biguanide;
1-[3-(4-chloro-2-trifluoromethoxyphenoxy)propyloxy]-5-isopropyl biguanide, mono phosphate salt;
1-[3-(4-chloro-2-trifluoromethoxyphenoxy)propyloxy]-5-isopropyl biguanide, bis phosphate salt;
1-[3-(2,4-bis(trifluoromethoxy)phenoxy) propyloxy]-5-isopropyl biguanide;
1-[3-(4-chloro-3-trifluoromethoxy phenoxy)propyloxy]-5-isopropyl biguanide;
1-[3-(4,5-dichloro-2-trifluoromethoxy phenoxy)propyloxy]-5-isopropyl biguanide;

1-[3-(2,2,3,3-Tetrafluoro-2,3-dihydro-benzo[1,4]dioxin-6-yloxy)propyloxy]-5 isopropyl biguanide;
1-[3-(2,2-Difluoro-benzo[1,3]dioxol-5-yloxy) propyloxy]-5-isopropyl biguanide;
1-[3-(4-(trifluoromethanethio)phenoxy)propyloxy[-5-isopropyl biguanide;
1-[3-(4-(trifluoromethanesulfonamido)phenoxy)propyloxy]-5-isopropyl biguanide; and
1-[3-(4-(trifluoromethanesulfonyl)phenoxy)propyloxy]-5-isopropyl biguanide.

In certain embodiments, the invention is directed to compositions, comprising:
at least one compound of formula I or XIII or a pharmaceutically acceptable salt thereof; and
at least one pharmaceutically acceptable carrier.

Such compositions are prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The water solubility of the hydrochloride salts and most other salts of the parent compounds may be limited, so when solutions are required it may be preferable to add solubilizing agents to the water, such as non-aqueous solvents. Alternatively, a more soluble salt may be used or a very dilute solution prepared.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Oral formulations are preferred and this invention has the advantage over related products of being readily absorbed by mammals at sufficient levels to make the compounds of the present invention orally active as therapeutic agents. Formulations for oral or injected use are based on sufficient solubility as to allow the therapeutic agent to enter solution in the stomach or in an injectable medium. Suitable drug formulations include, but are not limited to, tablets, pills, capsules, sachets, granules, powders, chewing gums, suspensions, emulsions, suppositories, and solutions. Particularly preferred for oral use are tablets and capsules of all varieties and microbe-free solutions for injection or infusion. Where appropriate and necessary the formulations may include diluents, binding agents, dispersing agents, surface-active agents, lubricating agents, coating materials, flavoring agents, coloring agents, controlled release formulations, sweeteners or any other pharmaceutically acceptable additives, for example, gelatin, sodium starch glycolate, lactose, starch, talc, magnesium stearate, microcrystalline cellulose, Povidone, hydrogenated or unsaturated oils, polyglycols, syrups or other aqueous solutions. Where the formulations are tablets or capsules and the like the formulations may be presented as premeasured unit doses or in multidose containers from which the appropriate unit dose may be withdrawn.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

The injectable form may be an aqueous or nonaqueous solution, suspension or emulsion in a pharmaceutically acceptable liquid, e.g. sterile pyrogen-free water or parenterally acceptable oils or mixture of liquids which may contain bacteriostatic agents, antioxidants or other preservatives and stabilizers, buffers (preferably but not limited to a physiological pH range of 6.5-7.7, solutes to render the solution isotonic with the blood, thickening agents, suspending agents or other pharmaceutically acceptable additives. Such forms will be presented in unit dose form such as ampules or disposable injection devices or in multi-dose forms such as a bottle from which the appropriate dose may be withdrawn, or as a solid form or concentrate that can be used to quickly prepare an injectable formulation. All formulations for injection are preferable as sterile and pyrogen free. Suppositories containing the compound will also contain suitable carriers, e.g. cocoa butter, polyglycols or other state-of-the-art carriers.

Preferably, the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In addition to standard pharmaceutical additives there may be included within formulations of the compound other therapeutic agents, particularly including other antimalarial agents and antiinfective agents. The compounds of formula I and formula XIII may be combined with sulfonamides or sulfones to improve the biological spectrum and potency of these compounds of formula I or formula XIII.

The compounds of the present invention may be prepared in a number of ways well known to those skilled in the art of which the following generally applicable multi-step process is preferred. This multi-step process typically utilizes readily available starting materials. Intermediate products, if commercially available, may simplify or obviate some of the process steps. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

In one embodiment, the invention is directed to processes for preparing antimicrobial compounds, comprising the steps of:

contacting a compound of formula II:

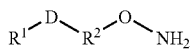

II with a compound of formula III:

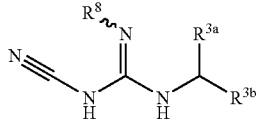

III for a time and under conditions sufficient to provide a compound of formula I:

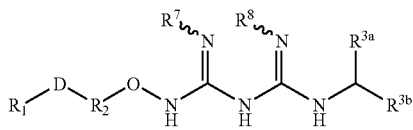

I wherein:

$R^1$ is $R^x$, substituted aryl, substituted alkyl, substituted fused cycloalkylaryl, substituted aralkyl, substituted cycloalkylarylalkyl, substituted heteroaryl, or substituted heteroarylalkyl, wherein the latter seven groups are substituted with at least one substituent selected from the group consisting of —CN, —OCF$_3$, haloalkoxy, —SR$^4$, —OCF$_3$, —SCF$_3$, haloalkylthio, —NR$^5$R$^6$, —SO$_2$R$^4$, —SO$_2$NR$^5$R$^{6a}$, heteroaryl, heterocyclyl or $R^{10}O$—(CH$_2$CH$_2$O)$_j$—, or combinations thereof;

$R^x$ is substituted or unsubstituted:

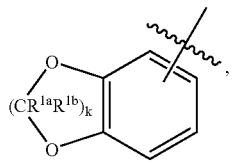

wherein each $R^{1a}$ and $R_{1b}$ are independently H, alkyl or fluoro;

$R^2$ is branched or straight chain lower alkylidene, or lower alkylene;

$R^{3a}$ and $R^{3b}$ are each independently hydrogen, lower alkyl, lower alkenyl, lower alkynyl, or taken together form a cycloalkyl or spiroalkyl group;

each $R^4$ is independently hydrogen, lower alkyl, substituted lower alkyl, lower alkenyl, substituted lower alkenyl, lower alkynyl, substituted lower alkynyl, aryl, substituted aryl, haloaryl, acyl, or heterocyclyl;

each $R^5$ is independently hydrogen, alkyl, substituted lower alkyl, lower alkenyl, substituted lower alkenyl, lower alkynyl, substituted lower alkynyl, alkyl substituted aryl, or acyl;

each $R^6$ is independently hydrogen, alkyl, substituted lower alkyl, lower alkenyl, substituted lower alkenyl, lower alkynyl, substituted lower alkynyl, alkyl substituted aryl, acyl, —SO$_2$R$^5$, or SO$_2$NR$^5$R$^5$; or $R^5$ and $R^6$ taken together with the atom to which they are attached form a heterocycle;

each $R^{6a}$ is independently hydrogen, alkyl, substituted lower alkyl, lower alkenyl, substituted lower alkenyl, lower alkynyl, substituted lower alkynyl, alkyl substituted aryl, acyl; or $R^5$ and $R^{6a}$ taken together with the atom to which they are attached form a heterocycle;

$R^7$ and $R^8$ are each, independently, hydrogen, alkyl, or acyl;

D is lower alkylidene, lower alkylene, —O—, —S—, or —N(R$^9$)—;

$R^9$ is hydrogen, alkyl, substituted lower alkyl, lower alkenyl, substituted lower alkenyl, lower alkynyl, substituted lower alkynyl, alkyl-substituted aryl, or acyl;

$R^{10}$ is alkyl or haloalkyl;

j is an integer from 1 to 20; and k is an integer from 1 to 4;

or a pharmaceutically acceptable salt thereof.

Yet more preferred in the above process for the production of the compound of the formula IV, $R^1$ is para-trifluoromethoxyphenyl, $R^2$ is —CH$_2$CH$_2$CH$_2$—, $R^{3a}$ and $R^{3b}$ are each independently methyl, or taken together form a cycloalkyl group, $R^7$ and $R^8$ are each, independently, H, and D is —O—. In other more preferred embodiments in the above process for the production of the compound of the formula IV, $R^1$ is 4-trifluoromethanethiophenyl, 4-trifluoromethanesulfonylphenyl, or 4-trifluoromethanesulfonamidophenyl $R^2$ is —CH$_2$CH$_2$CH$_2$—, $R^{3a}$ and $R^{3b}$ are each independently methyl, or taken together form a cycloalkyl group, $R^7$ and $R^8$ are each, independently, H, and D is —O—.

In other preferred embodiments of the process for production of the compound of formula IV, a compound of formula XIV:

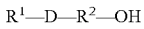

XIV is contacted with an alcohol halogenation agent or alcohol sulfonation agent for a time and under conditions effective to provide the compound of the formula IV. More preferably, in the production of a compound of formula IV as described directly above from a compound of formula XIV, the compound of formula XIV is produced by contacting a compound of the formula VI:

VI with a compound of the formula XV:

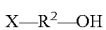

XV wherein:

X is halo, methanesulfonate, or para-toluenesulfonate; and $R^2$ is —(CH$_2$)$_n$—, wherein n is 2 to 10;

for a time and under conditions sufficient to provide the compound of the formula XIV. In certain preferred embodiments of the process for the production of a compound of formula XIV described directly above, $R^1$ is 2-chloro-4-trifluoromethoxy-phenyl or 4-chloro-2-trifluoromethoxyphenyl, $R^2$ is —$CH_2CH_2CH_2$—, $R^{3a}$ and $R^{3b}$ are each independently methyl, or taken together form a cycloalkyl group, $R^7$ and $R^8$ are each, independently, H, and D is —O—. In other preferred embodiments of the process for the production of a compound of formula XIV described directly above, $R^1$ is 2,4-bis-trifluoromethoxyphenyl, 4-chloro-3-trifluoromethoxyphenyl or 4,5-dichloro-2-trifluoromethoxyphenyl, $R^2$ is —$CH_2CH_2CH_2$—, $R^{3a}$ and $R^{3b}$ are each independently methyl, or taken together form a cycloalkyl group, $R^7$ and $R^8$ are each, independently, H, and D is —O—.

The route shown directly below is valid where D is —O—, —S—, or —$N(R^9)$— and $R^8$ is hydrogen or acyl in the intended compound (Ia). Where the starting material is an alkanol (VI), an excess of the alkanol is utilized and the desired reactant quantity is treated with one equivalent of alkali metal sodium to form the alkali metal salt in alkanolic solution.

In instances where the desired phenol is not commercially available, it may be prepared, for example, from the corresponding aromatic amine through its diazonium ion. (See F. A. Carey and R. J. Sundberg, *Advanced Organic Chemistry, Part B: Reactions and Synthesis*, $3^{rd}$ Ed., p. 588-591, Plenum Press, New York (1990) and R. C. Larock, Comprehensive Organic Transformations, VCH Publishers, New York, (1989)

In the case of amines, thiols, or phenols (VI), an excess of base is utilized, suitably aqueous alkali hydroxide or alkali carbonate. An excess of dihaloalkane, di-methanesulfonate, or di-para-toluenesulfonate (VII) is then added, suitably a 2-fold excess over the calculated amount of VI. When an aqueous solution is employed, a surfactant or phase transfer agent may be added to enhance the interaction of the phases. The mixture is heated with stirring at a temperature in the range of about 50° C. to about 100° C. for a time in the range of about 1 hour to about 48 hours, preferably about 12 hours to about 48 hours. The mixture is cooled, and the organic layer is separated. Distillation under reduced pressure, or separation by column chromatography provides the desired oxy-, amino-, or thioalkyl halide (IV), its corresponding methanesulfonate, or para-toluenesulfonate.

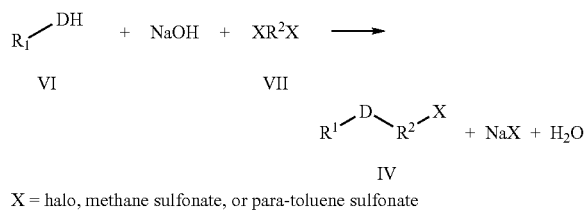

X = halo, methane sulfonate, or para-toluene sulfonate

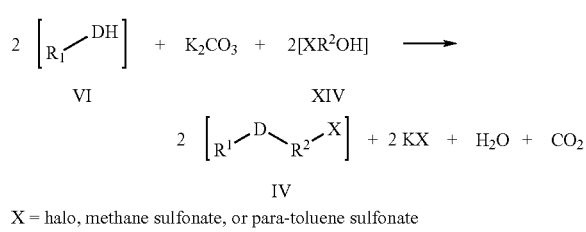

X = halo, methane sulfonate, or para-toluene sulfonate

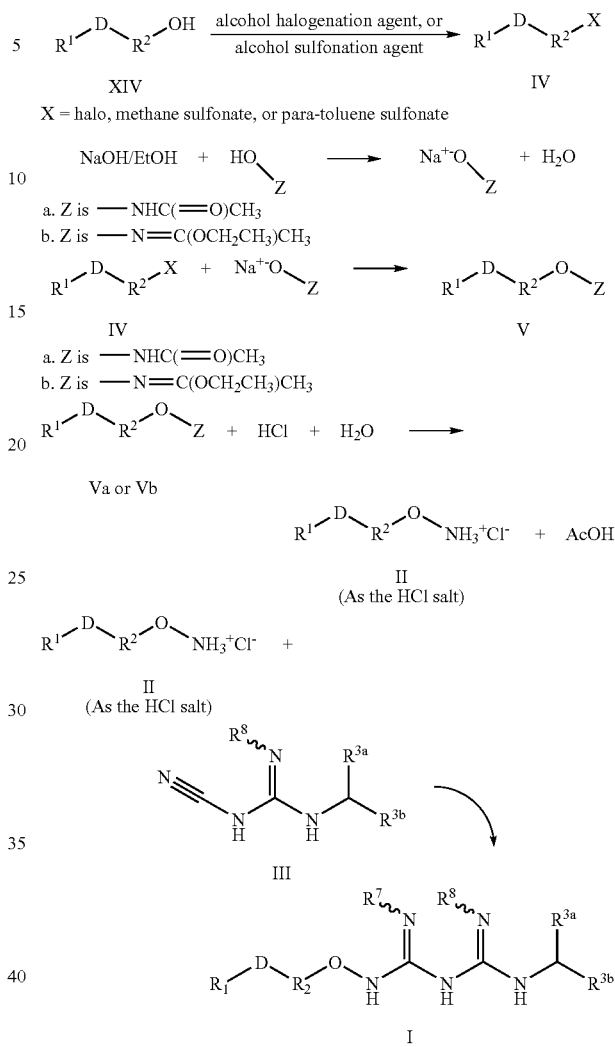

Alternatively, the desired oxy-, amino-, or thioalkyl halide (IV), or its corresponding methanesulfonate, or para-toluenesulfonate may be prepared by contacting a compound of the formula XIV with an alcohol halogenation agent or alcohol sulfonation agent. Non-limiting examples of typical reagents or conditions of use can be found in Larock, R. C. *Comprehensive Organic Transformations*, VCJ Publishers, Inc. NY, 353-363 (1989) and Greene, T. W. and Wuts, P. G. M. *Protective Groups in Organic Synthesis*, $2^{nd}$ Ed., John Wiley & Sons, Inc. NY, 117-118 (1991), incorporated herein by reference, in their entireties. The compound of formula XIV may be prepared by contacting a compound of the formula VI with a compound of formula XV (X—$R^2$—OH), wherein $R^2$ is $C_2$—$C_{10}$ alkylene, for a time and under conditions similar to those utilized in the production of a compound of formula IV through contacting of a compound of formula VI with a compound of formula VII.

Acetohydroxamic acid, N-hydroxyacetimidate, or a functional equivalent is converted into the corresponding alkali metal salt in an alcohol solution by addition of base. Suitable bases include those bases which can effectively deprotonate the acidic proton in acetohydroxamic acid, and include, but are not limited to, NaOH, KOH, alkali metal salts of alkanols, alkali metal carbonates, KH, NaH, and the like. The oxy-, amino-, or thioalkyl halide (IV), or its corresponding methanesulfonate, or para-toluenesulfonate, produced as above, is then added and the mixture heated to a temperature in the range of about 45° C. to 70° C. for a time in the range of about 1 to 24 hours, preferably between about 12 to 24 hours. The solvents are removed under reduced pressure and the residue is partitioned between water and a water-immiscible, organic solvent. The organic solvent is dried, filtered, and evaporated to give the anticipated oxy-, amino-, or thioalkyl acetohydroxamate (Va) or imidate derivative (Vb).

The acetohydroxamate hydrochloride(Va) or imidate derivative (Vb) is taken up in an alkanol, optionally with an excess of dilute mineral acid added, suitably hydrochloric acid, preferably without excess acid, and the mixture is heated under reflux for a time in the range of about 2 to about 24 hours, preferably about 16 hours, and the solvents are removed under reduced pressure to give the desired alkoxyamine (II, as its hydrochloride salt).

The alkoxyamine hydrochloride (II) is taken up in an alkanol and the appropriate omega-substituted dicyandiamide (III), for example, a lower alkyl dicyandiamide, is added. The mixture is heated under reflux for a time in the range of about 4 to about 24 hours. The resulting solution may be diluted with water, basified and extracted with an organic water-immiscible solvent to provide, after removal of solvents under reduced pressure, the desired alkoxy omega-substituted iminodicarbonimidic diamide (Ia) as a free base. Alternatively, the resulting alkanolic solution can be evaporated under reduced pressure to give the desired alkoxy omega-substituted iminodicarbonimidic diamide (Ia) as its hydrochloride salt or salt hydrate (Ia), which can be purified by column chromatography or by crystallization. Where reagent (III) is a mono omega-substituted dicyandiamide carrying no substitution on the remaining imino nitrogen, then $R^8$ in compound III is hydrogen and, in the thus obtained product of formula I, $R^7$ and $R^8$ will be hydrogen.

Where it is desired either to place the same substituent at $R^7$ and $R^8$ or where $R^8$ is other than hydrogen, and a substituent is desired at $R^7$, the hydrochloride hydrate of Ia is suspended in a suitable water-immiscible, reaction-inert organic solvent, suitably ethyl acetate, shaken with an excess of aqueous alkali, suitably aqueous sodium hydroxide, the organic layer is separated, dried, and heated under reflux for from about 1 hours to about 4 hours with an excess of a suitable acylating agent, for example, acetyl chloride. After completion of the reaction, the volatile components are removed under reduced pressure to yield the desired acylated compound.

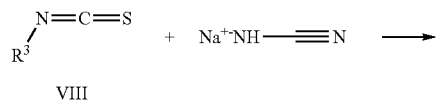

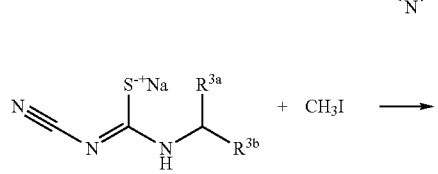

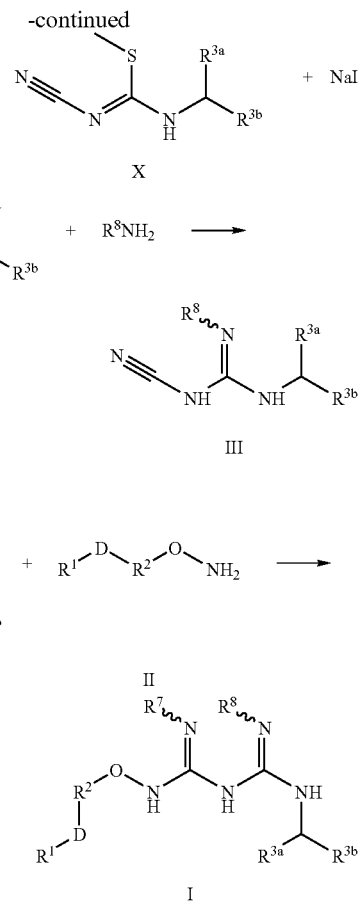

Where $R^8$ is alkyl, a different synthetic route is desirable, as illustrated above. For example, see Curd, F. H. S., et al. *J. Chem. Soc.* 1630-45 (1948) and Davidson, J. S., *Chemistry and Industry*, 1977-8 (1965).

The $R^3$ isothiocyanate (VIII) is added to a suspension of sodium cyanamide in alkanol, such as ethanol, which precipitates the sodium salt of 3-cyano-1-$R^3$-isothiourea (IX). After filtering off the sodium salt and washing it with alkanol, methyl iodide is added to the filtrate with rapid stirring at ambient temperature. The product separates. The suspension is cooled in an ice bath, the solids filtered off, washed with water and dried to give 3-cyano-S-methyl-1-$R^3$-isothiourea (X).

The isothiourea (X) is added to an alkanolic solution of $R^8$ alkylamine and the mixture is heated for 4 hours in a pressure bottle at about 50° C. The resulting clear solution is gradually diluted with water (75 ml) and product crystallizes out to give the $N^1$-cyano-$N^3$—CHR$^{3a}$R$^{3b}$—$N^2$—$R^8$-guanidine (III). This can then be reacted with the hydroxylamine hydrochloride salt (II) as described previously to obtain the desired compound (Ia).

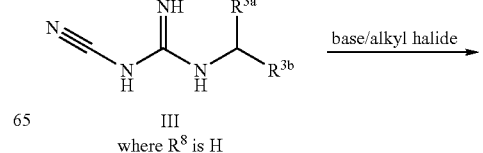

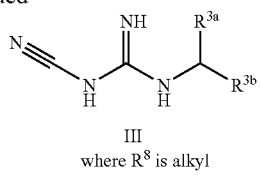

III
where R⁸ is alkyl

Alternatively, the appropriate omega-substituted dicyandiamide (III), for example, a lower alkyl dicyandiamide, may be reacted with an alkyl halide in the presence of base to provide the corresponding alkylated omega-substituted dicyandiamide (III). This may then be reacted as described, supra, to yield a compound of formula I.

This reaction can be carried out in the absence or presence of solvent, as one skilled in the art would recognize. Preferably this is carried out in the presence of an aprotic solvent. Non-limiting examples of aprotic solvents include hydrocarbon solvents, and halogenated derivatives thereof, such as cyclohexane, pentane, toluene, benzene, cycloheptane, methylcyclohexane, ethylbenzene, m-, o-, or p-xylene, octane, indane, nonane, dichloromethane, chloroform, and the like. Aprotic solvent further include ethers such as diethyl ether, dimethoxymethane, tetrahydrofuran (THF), 1,3-dioxane, 1,4-dioxane, furan, ethylene glycol dimethyl ether, ethylene glycol diethyl ether, diethylene glycol dimethyl ether, diethylene glycol diethyl ether, trieithylene glycol diisopropyl ether, anisole, or t-butylmethyl ether. Other aprotic solvents include, for example, N,N-dimethylformamide (DMF), N,N-dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (MeCN), dimethylsulfoxide (DMSO), propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, and hexamethylphosphoramide.

The compounds of the present invention may be made in the form of the monohydrohalic acid addition salts and/or the solvated compound, for example the hydrochloride hydrate or the hydrobromide. Other salts may be made however by simple reaction of a base with acid and may be desirable in order to modify the properties of the product, such as its toxicity, taste, physical form, or rate of release into the body. For example, the compounds may be made in the form of the sulfate, bisulfate, phosphate, nitrate, acetate, maleate, phthalate, succinate, phosphate, nitrobenzoate, stearate, mandelate, N-acetyl-glycinate, pamoate, sulfonate, di-sulfonate, cyclohexyl sulfamate, citrate, tartrate, propionate, glycolate, lactate, malate, ascorbate, hydroxymaleate, phenylacetate, glutamate, benzoate, salicylate, sulfanilate, 2-acetoxybenzoate, fumarate, toluenesulfonate, methanesulfonate, ethane disulfonate, isethionate, mesylate or gluconate, and the like.

Stable salts are normally formed with a ratio of one molecule of $N^1,N^5$-disubstituted imidodicarbonimidic diamides to one or two molecules of monoprotic acid (or more than one molecule of compound Ia in the case of polyprotic acids) but the possibility of having basic groups as substituents in $R^1$, for example, means that further quantities of acid may be combined with the disubstituted imidodicarbonimidic diamide in some cases. In addition the above molecules may contain various hydrated forms with molecules of water or other solvent included in the molecular formula of the stable entity.

The presence of the imino biguanide nitrogens on the molecule creates the possibility of forming acyl derivatives by reaction with appropriate substrates.

The dihydrotriazine compounds of formula XIII may be prepared enzymatically by the oxidative cyclization of the $N^1,N^5$-substituted asymmetrical imidodicarbonimidic diamides of the invention. The cyclization may occur naturally in vivo via metabolic processes. The cyclization may also be carried out in vitro with the appropriate microbes or enzymes.

Alternatively, the dihydrotriazine compounds of formula XIII may be prepared synthetically by reacting alkoxyamine (II), as its hydrochloride salt, with sodium dicyandiamide (XI) in an alkanol or other appropriate solvent. The product alkoxydicyandiamide (XII) is treated with a mineral acid, such as hydrochloric acid, in an alkanol, such as methanol, and ketone, such as acetone, or a cyclopropanone equivalent, such as 1-trimethylsilyloxy-1-ethoxy cyclopropane. The reaction may be conducted at 10° C.-50° C., preferably ambient temperature, and for 0.5 hours-10 hours, preferably one hour. The product (XIII where $R^7$ and $R^8$=H) may be isolated by trituration with a solvent, such as acetone, or by column chromatography.

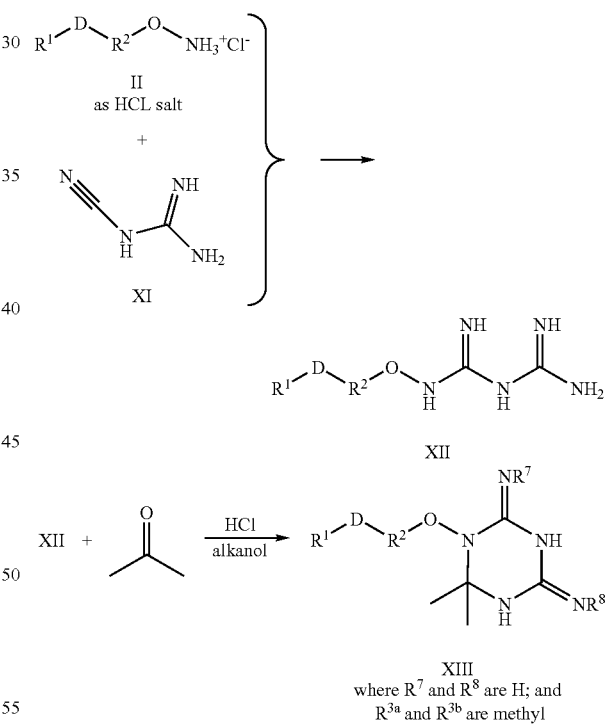

XIII
where $R^7$ and $R^8$ are H; and
$R^{3a}$ and $R^{3b}$ are methyl

While the biguanide derivatives of formula I have inherent biological activity, these compounds, in part, owe their in vivo pharmacological activity to the metabolic conversion of the biguanide to its corresponding dihydrotriazine metabolite (XIII). Dihydrotriazines have been shown to be potent inhibitors of dihydrofolate reductase (DHFR) and, as such, are effective as therapeutic agents, including but not limited to antimicrobial agents.

In certain preferred embodiments, the dihydrotriazines of the invention (compounds of formula XIII) may be employed in an in vitro method to evaluate and predict the biological activities of their predecessor biguanides (i.e., the biguanides of formula I are prodrugs of the dihydrotriazine of formula XIII). These prodrugs do not exhibit the full extent of their biological activity until they are converted to their dihydrotriazine counterparts in vivo, and thus may not be readily evaluated in vitro. However, the biguanide derivatives of formula I may be evaluated in vitro by assaying for the activity of their corresponding dihydrotriazines.

In one embodiment, the invention is directed of methods evaluating the in vivo biological activity of a compound of formula I:

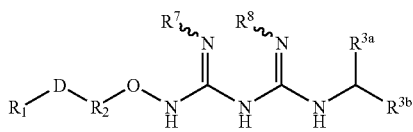
I wherein:
$R^1$ is $R^X$, substituted aryl, substituted alkyl, substituted fused cycloalkylaryl, substituted aralkyl, substituted cycloalkylarylalkyl, substituted heteroaryl, or substituted heteroarylalkyl, wherein the latter seven groups are substituted with at least one substituent selected from the group consisting of —CN, —OCF$_3$, haloalkoxy, —SR$^4$, —OCF$_3$, —SCF$_3$, haloalkylthio, —NR$^5$R$^6$, —SO$_2$R$^4$, —SO$_2$NR$^5$R$^{6a}$, heteroaryl, heterocyclyl or $R^{10}$O—(CH$_2$CH$_2$O)$_j$—, or combinations thereof;

$R^x$ is substituted or unsubstituted:

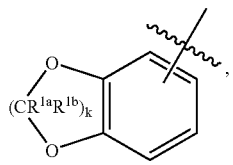

wherein each $R^{1a}$ and $R^{1b}$ are independently H, alkyl or fluoro;
$R^2$ is branched or straight chain lower alkylidene, or lower alkylene;
$R^{3a}$ and $R^{3b}$ are each independently hydrogen, lower alkyl, lower alkenyl, lower alkynyl, or taken together form a cycloalkyl or spiroalkyl group;
each $R^4$ is independently hydrogen, lower alkyl, substituted lower alkyl, lower alkenyl, substituted lower alkenyl, lower alkynyl, substituted lower alkynyl, aryl, substituted aryl, haloaryl, acyl, or heterocyclyl;
each $R^5$ is independently hydrogen, alkyl, substituted lower alkyl, lower alkenyl, substituted lower alkenyl, lower alkynyl, substituted lower alkynyl, alkyl substituted aryl, or acyl;
each $R^6$ is independently hydrogen, alkyl, substituted lower alkyl, lower alkenyl, substituted lower alkenyl, lower alkynyl, substituted lower alkynyl, alkyl substituted aryl, acyl, —SO$_2$R$^5$, or SO$_2$NR$^5$R$^5$; or $R^5$ and $R^6$ taken together with the atom to which they are attached form a heterocycle;

each $R^{6a}$ is independently hydrogen, alkyl, substituted lower alkyl, lower alkenyl, substituted lower alkenyl, lower alkynyl, substituted lower alkynyl, alkyl substituted aryl, acyl; or $R^5$ and $R^{6a}$ taken together with the atom to which they are attached form a heterocycle;
$R^7$ and $R^8$ are each, independently, hydrogen, alkyl, or acyl;
D is lower alkylidene, lower alkylene, —O—, —S—, or —N(R$^9$)—;
$R^9$ is hydrogen, alkyl, substituted lower alkyl, lower alkenyl, substituted lower alkenyl, lower alkynyl, substituted lower alkynyl, alkyl-substituted aryl, or acyl;
$R^{10}$ is alkyl or haloalkyl;
j is an integer from 1 to 20; and
k is an integer from 1 to 4;
or a pharmaceutically acceptable salt thereof;

comprising the step of:
assaying in vitro for the biological activity of the product of the oxidative cyclization of the compound of formula I.

There is disclosed an improved mode of prophylaxis and treatment of infections by one or more of plasmodia; mycobacteria; toxoplasmosis; and pneumocystis organisms; and agents causing nocardia infections. The biguanide derivatives of formula I, and the corresponding dihydrotriazines of formula XIII, of the present invention, their salts and derivatives thereof have antimalarial and antibacterial activity, as well as effectiveness against some fungi, protozoans, parasites and viruses. Additionally, the biguanide derivatives of formula I or XIII exhibit similar activities. In particular, these disubstituted asymmetrical biguanides, the corresponding dihydrotriazines, and salts, as well as their substituted derivatives, exhibit antiparasitic activity including activity against the plasmodia of malaria (*P. berghei*), exhibit antimicrobial activity against mycobacteria including, but not limited to, *M. avium* intercellulare, *M. avium* complex, *M. tuberculosis, M. leprae* and *Toxoplasma gondii*, and pneumocystis organisms such as *P. carinii* associated with, but not limited to, immuno-compromised patients. In addition, these compounds have activity against nocardia infections.

In yet other embodiments, the invention is directed to methods for reducing in a patient the level of infection caused by an organism selected from the group consisting of *Plasmodium* sp., *Mycobacterium* sp., *Toxoplasma gondii*, and *Pneumocystis carinii*, comprising the step of:
administering to said patient in need thereof an effective amount of at least one compound of formula I or formula XIII.

In yet further embodiments, the invention is directed to methods for protecting a patient susceptible to infection caused by exposure to an organism selected from the group consisting of *Plasmodium* sp., *Mycobacterium* sp., *Toxoplasma gondii*, and *Pneumocystis carinii*, comprising the step of:
administering to said patient in need thereof an effective amount of at least one compound of formula I or formula XIII.

The preferred dosage range is between 0.5 and 10 mg/kg/day. The range is quite large because the physician must use his/her judgment on whether the dosage is prophylactic and if given to an infected subject, on what the level of infection is. When given as tablets the tablets may contain 25-500 mg of active material.

EXAMPLE OF BIOLOGICAL ACTIVITY OF THE INVENTION

Biological Activity Against *Plasmodium berghei* (KGB Strain)

Mouse Malaria Model:

Selective compounds of this invention were tested for antimalarial activity in the established modification of the Thomson model. Jensen, et al., *J Med. Chem.*, 2001, 44, 3925-3931 as follows: CD-1 mice (male and/or female), 4 to 5 weeks old, are purchased from Charles River. Seven (7) mice are typically used in each experimental group. The mice are housed 3 to 4 per cage and are maintained at a temperature of 75° C. with a 12-hour day light cycle. The mice are fed a standard Ralston Purina® mouse chow and given water ad. lib. Their cages and water bottles were changed twice a week.

Preparation of the test compounds oral administration involved grinding the material with a mortar and pestle before diluting in 0.5% hydroxyethylcellulose-Tween 80 (polyoxyethylene (20) sorbitan mono-oleate) for oral administration. For subcutaneous administration, the test compounds were suspended in peanut oil.

The mice were infected intraperitoneally with 50,000 red blood cells infected with a drug-sensitive strain of *Plasmodium berghei* (KBG strain) on day 0. The inoculum was obtained from a donor mouse having a parasitemia between 5% and 10%.

The compounds were administered according to the weight of the mice. The mice were weighed each day before the drugs were administered. Test compounds are given in a volume of 10 ml/kg of body weight. Compounds were administered either orally or subcutaneously twice a day (6 hours apart) for 3 days starting on the 3rd day post infection. Blood films were taken on day 6 post-infection and twice weekly for 30 days. The level of parasites (parasitemia) was determined from the Giemsa stained blood films.

Antimalarial activity was quantified by a percent survival calculated for each treated group on Day 31. The infected non-treated control mice usually die between days 7 and 10. The results are shown in Table 1.

TABLE 1

| TEST GROUP | % SURVIVAL AT DAY 31 DOSE (mg/kg) | | | | |
|---|---|---|---|---|---|
| | 64 | 32 | 16 | 8 | 4 |
| Infected Non-Treated Controls | 0 | 0 | 0 | 0 | 0 |
| Compound of Example 5 | 100 | 100 | 86 | 14 | 0 |
| Compound of Example 6 | 100 | 71 | 43 | 14 | 0 |

Biological Activity Against *Mycobacterium* Isolates

Antituberculosis activities were assessed in vitro using the biologically active dihydrotriazine metabolites of the imidodicarbonimidic diamides. The assay methodology is detailed as follows:

To tissue culture treated 96-well microtiter plates were added 20 μl of a solution of test compound. The plates were allowed to dry in an incubator at a temperature between 50° to 60° C. for 20 to 30 minutes. Then the plates were subjected to UV light for 15 minutes to kill bacteria. The plates were generally used within 2-3 days of being made. To each well was added 100 μl of culture broth and the appropriate strain of *Mycobacterium tuberculosis* or *Mycobacterium avium*. The plates were then incubated at 37° C. for between 18 days to 21 days. Growth was assessed by turbidity measurement and MICs reported in μg/ml.

TABLE 2

Inhibitory Activity of Dihydrotriazine Metabolites of PS Series Prodrugs

| | MIC of WR99210 Metabolite of PS-15[a] Mg/ml | MIC of Metabolite of PS-26[b] μg/ml | MIC of Metabolite of Compound of Example 5 μg/ml |
|---|---|---|---|
| Strain of *Mycobacterieum avium* | | | |
| 101 | 19.5 ± 37.7 | 1.95 ± 1.63 | 3.1 |
| LPR | 38.4 ± 32.9 | 16.6 ± 11.7 | 37.5 ± 17.7 |
| Farino | <0.1 | <0.1 | 1 ± 0.85 |
| 3404-4 | 15.6 ± 13.3 | 0.4 | 0.6 ± 0.3 |
| Strain of *Mycobacterium tuberculosis* | | | |
| Erdmann | 2.2 | | 19 |

(a) PS-15

(b) PS-26

The invention is further described in the following examples. All the examples are actual examples. These examples are for illustrative purposes only, and are not to be construed as limiting the appended claims.

EXAMPLES

The following experimental details apply to examples below. All chemicals were reagent grade and used without further purification. Melting points were determined on a Laboratory Devices Mel-Temp II heating block type melting point apparatus and are uncorrected. TLC was performed on Baker Si250F$_{254}$ silica gel plates using UV/fluorescence visualization. Visualization was, where noted, also aided by the use of a diazonium salt spray prepared by dissolving 4-nitroaniline (1.0 g) in 2N HCl (200 mL). An aliquot of this solution was then titrated to colorlessness with 2N sodium nitrite just prior to use as a spray. After the spraying with the diazonium spray, the plate was sprayed with a 5% sodium carbonate solution to develop the TLC spots. A TLC eluent found to be useful for the biguanides and triazines was a 12:6:3:2 mixture of CHCl$_3$/acetone/n-butanol/formic acid. Aldrich Chemical Co. 200-400 or 70-230 mesh 60 Å silica gel was used for column chromatography. Elemental analyses were done by Robertson Microlit of Madison, N.J.

Example 1

Preparation of 1-(3-(4-trifluoromethoxy)phenoxy)propyl bromide, a compound of the formula IV A mixture of 4-trifluoromethoxyphenol (5.0 g, 28 mmol), 1,3-dibromopropane (28 g, 40 mmol), sodium hydroxide (7.0 g of a 24% aqueous solution), and tetrabutylammonium hydrogen sulfate (0.2 g) was stirred at 70° for 48 hours. The reaction layers were allowed to separate. Excess 1,3-dibromopropane was removed from the organic phase under high vacuum at a bath temperature of 100° C. to give 8.5 g of crude product (102%, based on expected weight recovery).

Example 2

Preparation of 2-(3-(4-trifluoromethoxyphenoxy)propyl acetohydroxamate, a compound of Formula V The crude bromide (8.5 g) from Example 1 was heated at 55° C. with potassium acetohydroxamate (4.75 g, 42 mmol) in 20 ml of ethanol for 16 hours. The crude solution was evaporated on a rotary evaporator, diluted with water (20 ml), and extracted with ethyl acetate (2×25 ml). The combined organic extracts were dried over anhydrous potassium carbonate, filtered, and the solvent evaporated to give 7.0 g of product as an oil. The obtained material was used without further purification in the following example.

Example 3

Preparation of 3-(4-trifluoromethoxyphenoxy)propyloxy)amine hydrochloride, a compound of the formula II (as its HCl salt)

Crude acetohydroximate (7.0 g, 24 mmol), from Example 2, was dissolved in 50 ml of methanol, and 12M hydrochloric acid (3.5 grams, 35.5 mmol) and water (3.5 grams (194 mmol) were added. The reaction mixture was maintained with stirring at room temperature for 16 hours. The solvent was evaporated using a rotary evaporator. Residual solvent was removed from the crude product under high vacuum (1.0 torr) to provide 6.8 grams of 3-(4-trifluoromethoxyphenoxy)propyloxy)amine hydrochloride. The obtained material was used without further purification in the following synthetic step.

Example 4

Preparation of 1-(3-(4-trifluoromethoxyphenoxy)propyloxy)-5-isopropyl biguanide, a compound of the formula I 3-(4-Trifluoromethoxyphenoxy)propyloxy)amine hydrochloride from Example 3 (6.8 grams, 23.6 mmol) and isopropyldicyandiamide (3.0 grams, 23.8 mmol) were added to ethyl acetate (50 ml) and heated to 60° C. for 16 hours. The solution was cooled, diluted with ethyl acetate (50 ml) and basified with sodium hydroxide (10 ml of 24% aqueous solution). The organic phase was separated, dried over potassium carbonate, filtered, and the solvent evaporated to afford crude biguanide (8.3 grams). The product was subjected to column chromatography on 70-230 mesh silica gel utilizing ethyl acetate:ethanol (4:1) as eluent. The appropriate fractions were combined and the solvent evaporated to give 6.6 grams of 1-(3-(4-trifluoromethoxyphenoxy)propyloxy)-5-isopropyl biguanide free base (62.5% overall yield from 4-trifluoromethoxyphenol).

Example 5

Preparation of 1-(3-(4-trifluoromethoxyphenoxy)propyloxy)-5-isopropyl biguanide hemisuccinate, a compound of the formula I (as its mono- hemisuccinate salt)

Succinic acid (1.05 g, 8.9 mmol) was added to a solution of 1-(3-(4-trifluoromethoxyphenoxy)propyloxy)-5-isopropyl biguanide free base (6.6 grams, 17.5 mmol) in 20 ml of ethanol. The mixture was heated to dissolve the acid and water (40 ml) was added. The solution was cooled to room temperature and subsequently refrigerated to complete crystallization. The crystals were isolated by filtration, washed with 5 ml of ice-cold 50% ethanol and dried to yield 1-(3-(4-trifluoromethoxyphenoxy)propyloxy)-5-isopropyl biguanide hemisuccinate (6.0 grams 78.5%), with melting point 154° C.-155° C. Elemental Analysis for $C_{17}H_{25}N_5O_5ClF_3$: Calculated: C; 46.78; H, 5.77; N, 16.04 Found: C; 46.85, H; 5.78, N; 15.86.

Example 6

Preparation of 1-(3-(4-trifluoromethoxyphenoxy)propyloxy)-5-cyclopropylbiguanide hydrochloride, a compound of the formula I (as its hydrochloride salt)

Cyclopropyl dicyandiamide (0.86 grams (6.96 mmol) was added to a solution of 3-(4-trifluoromethoxyphenoxy) propyloxyamine hydrochloride (2.0 grams (6.69 mmol) in 20 ml of absolute ethanol. The solution was refluxed with stirring at 65-70° C. overnight. After cooling and solvent removal by stripping, the reaction residue was then purified over a silica gel column using 10% methanol in ethyl acetate to give 1-(3-(4-trifluoromethoxyphenoxy)propyloxy)-5-cyclopropylbiguanide hydrochloride (1.7 g 65%). The product was recrystallized from ethanol-water to afford the crystalline salt (1.5 grams 54%): melting point 112° C.-116° C. Elemental Analysis for $C_{15}H_{21}N_5O_3ClF_3$: Found: C, 43.50; H, 5.04; N, 16.78; Cl, 8.2; Calculated: C, 43.74; H, 5.14; N, 17.00; Cl, 8.60.

Example 7

Preparation of 1-(3-(4-trifluoromethoxyphenoxy)propoxy)-biguanide, a compound of the formula XII 3-(4-Trifluoromethoxyphenoxy)propyloxyamine hydrochloride (7.2 g, 25 mmol) and dicyandiamide (2.3 g, 25 mmol) were dissolved in 50 ml of methoxyethanol and was heated to 75° C. and maintained overnight. The reaction mixture was evaporated, diluted with 10% aqueous sodium hydroxide and the precipitated oil separated. The oil was extracted with ethyl acetate, and the extract is removed of solvent in vacuo to give 7.6 g of crude free base (XII).

Example 8

Preparation of 6,6-Dimethyl-1-[3-(4-trifluoromethoxy-phenoxy)-propoxy][1,3,5]triazinane-2,4-diylidenediamine hydrochloride, a compound of the formula XIII (as its hydrochloride salt)

The obtained free base XII from Example 7 (3.4 g) was dissolved in 30 ml of methanol, 1.1 ml of concentrated hydrochloric acid, and 10 ml of acetone. The reaction mixture was maintained at room temperature overnight and then the solvent was removed under reduced pressure to give 4.1 g of crude product. The crude material was triturated with acetone overnight and the obtained crystals separated by filtration to give 1.4 g of the desired dihydrotriazine (XIII): m.p. 170° C.-172° C.; Elemental Analysis Found: C, 43.75; H, 5.14; N, 17.00; Calculated: C, 43.68; H, 5.22; N, 17.04.

Example 9

Preparation of 2-chloro-4-trifluoromethoxyphenol, a compound of the formula VI

A solution of 4-trifluoromethoxyphenol (20 g, 0.11 mole) and sulfuryl chloride (18.20 mL, 0.22 mole) was stirred at room temperature for five hours. The excess of sulfuryl chloride was evaporated by rotary evaporator. The residue was dissolved in 50 mL of dichloromethane and washed with 50 mL of $H_2O$. The organic layer was separated, dried over $MgSO_4$, filtered and concentrated to yield 22 g of the product. The crude product was purified over a silica gel column using 10% ethyl acetate in hexane to yield 16.4 g of the product. $^1$H-NMR (DMSO, 500-MHz), δ 10.59 (s, 1H), 7.43 (d, J=2.75 Hz, 1H), 7.18 (dd, $J_1$=2.75 Hz, $J_2$=7.16 Hz, 1H), 7.03 (d, J=7.16 Hz, 1H). MS (electro-spray) [M−H] 211.4.

Example 10

Preparation of 3-(2-chloro-4-trifluoromethoxyphenoxy)propanol a compound of the formula XIV To a solution of 2-chloro-4-trifluoromethoxyphenol (16.4 g, 0.077 mole) in 100 mL of acetonitrile was added 3-bromopropanol (12.87 g, 0.092 mole) and potassium carbonate (21.33 g, 0.154 mole). The resulted solution was refluxed at 75° C.-80° C. overnight. The solvent was then evaporated. The residue was dissolved in 100 mL of ethyl acetate and washed with 100 mL of $H_2O$. The organic layer was separated, dried over $MgSO_4$, filtered and the organic solvent was evaporated to yield 20 g of the product.

Example 11

Preparation of 3-(2-chloro-4-trifluoromethoxyphenoxy)propyl methane sulfonate, a compound of the formula IV To a solution of 3-(2-chloro-4-trifluoromethoxyphenoxy)-propanol (20 g, 0.074 mole) in 100 mL of dichloromethane at 0° C. was added methanesulfonyl chloride (6.83 mL, 0.089 mole) and triethylamine (20.5 mL, 0.148 mole). The resulting solution was stored in a refrigerator overnight. The solution was then washed with 100 mL of cooled, diluted $HCl$-$H_2O$ solution. The organic layer was separated, dried over $MgSO_4$, filtered and evaporated of solvent to yield 25.4 g of the product.

Example 12

Preparation of N-(3-(2-chloro-4-trifluoromethoxyphenoxy)propyloxy) ethyl acetimidate, a compound of the formula V To a solution of 3-(2-chloro-4-trifluoromethoxyphenoxy)-propyl methane sulfonate (25.4 g, 0.073 mole) in 100 mL of acetonitrile was added ethyl N-hydroxy acetimidate (9 g, 0.087 mole), potassium carbonate (20 g, 0.15 mole) and tetrabutyl-ammonium hydrogen sulfate (2.5 g, 0.007 mole). The resulting solution was refluxed at 70° C.-75° C. overnight. The solvent was then evaporated and the residue was dissolved in 100 mL of ethyl acetate. The solution was washed with 100 mL of $H_2O$. The organic layer was separated, dried over $MgSO_4$, filtered and evaporated of solvent to yield 20 g of the product. The crude product was purified over a silica gel column using 5% ethyl acetate in hexane to yield 14.7 g of the product.

Example 13

Preparation of 3-(2-chloro-4-trifluoromethoxyphenoxy)propyloxyamine hydrochloride, a compound of the formula II (as the hydrochloride salt)

To a solution of N-(3-(2-chloro-4-trifluoromethoxyphenoxy)-propyloxy)ethyl acetimidate (14.7 g, 0.041 mol) in 60 mL of absolute ethanol at 0° C. was added 6.9 mL of 12N HCl. The resultant solution was stored in a refrigerator overnight. The solvent was then evaporated and the crude product was recrystallized from hexane-ethyl acetate solvent to yield 12 g of the product. $^1$H-NMR (DMSO, 500 MHz), δ 11.03 (bs, 1H), 7.57 (d, J=2.85 Hz, 1H), 7.35 (dd, $J_1$=2.85 Hz, $J_2$=14.64 Hz, 1H), 7.26 (d, J=14.64 Hz, 1H), 4.19 (dd, 2H), 4.15 (dd, 2H), 2.10 (m, 2H). MS (electro-spray) [M+H]$^+$ 288.45.

Example 14

Preparation of 1-[3-(2-chloro-4-trifluoromethoxyphenoxy)propyloxy]-5-isopropyl-biguanide phosphate salt, a compound of the formula I A mixture of 3-(2-chloro-4-trifluoromethoxyphenoxy)-propyloxyamine hydrochloride salt (8.8 g, 0.027 mol) and isopropyl dicyandiamide (3.44 g, 0.027 mol) was heated for 30 minutes at 100° C.-110° C. The crude product was dissolved in 100 mL of ethyl acetate and washed with 100 mL of cooled 10% NaOH—$H_2O$ solution. The organic layer was separated, dried over $MgSO_4$, filtered and evaporated of solvent. The residue was then dissolved in 50 mL of absolute ethanol and 3.36 g of 85% phosphoric acid was added. The ethanol was evaporated and the crude product was recrystallized from water to yield 10 g of the crystalline product. Elemental analysis for $C_{15}H_{24}N_5O_7ClF_3P$: Calculated C, 35.34; H, 4.74; N, 13.74; Cl, 6.95; F, 11.18. Found: C, 35.53; H, 4.71; N, 13.69; Cl, 7.24; F, 11.57, $^1$H-NMR (DMSO, 500 MHz), δ 7.56 (d, 1H), 7.34 (dd, 1H), 7.25 (d, 1H), 4.19 (m, 2H), 3.96 (m, 2H), 3.71 (m, 1H), 2.05 (m, 2H), 1.12 (d, 6H), MS (electro-spray) [M+H]$^+$ 412.7. IR (KBr) 3507, 3398, 3115, 2974, 2943, 1675, 1276, 1220, 1193, 1058, 950 cm$^{-1}$. mp 92-94° C.

Example 15

Preparation of 1-[3-(4-chloro-2-trifluoromethoxyphenoxy)propyloxy]-5-isopropyl biguanide, bis phosphate salt, or mono phosphate salt, a compound of the formula I 1-[3-(4-chloro-2-trifluoromethoxyphenoxy)propyloxy]-5-isopropyl biguanide was prepared from 2-trifluoromethoxyphenol under substantially the same conditions utilized in the preparation of 1-[3-(2-chloro-4-trifluoromethoxyphenoxy)-propyloxy]-5-biguanide from 4-trifluoromethoxyphenol (Alfa Aesar, Ward Hill, Mass.) (See Examples 10 to 14). The crude product was recrystallized from ethyl acetate. Elemental analysis for $C_{15}H_{27}N_5O_{10}ClF_3P_2$ calculated C=29.64, H=4.47, N=11.52, Cl=5.83, F=9.37, Found C=29.81, H=4.31, N=11.44, Cl=5.65, F=9.73. $^1$H-NMR (DMSO, 500 MHz), δ 7.52 (d, 1H), 7.44 (dd, 1H), 7.28 (d, 1H), 6.25 (bs, 1H), 4.10 (m, 2H), 3.93 (m, 2H), 3.37 (m, 1H), 2.03 (m, 2H), 1.14 (m, 6H). MS (electro-spray) [M+H]$^+$=412.9 IR (KBr) 3498, 3454, 3386, 2985, 2961, 1670, 1296, 1218, 1063, 999 cm$^{-1}$. mp 125°-127° C.

The crude product was also crystallized from water to give the mono phosphate salt of the title compound: m.p. 115°-118° C.

Example 16

Preparation of 2,4-bis(trifluoromethoxy)phenol, a compound of the formula VI (a) 1-(bromodifluoromethoxy)-3-(trifluoromethoxy)benzene A solution of 3-trifluoromethoxyphenol (Alfa Aesar, Ward Hill, Mass.) and a suitable base in an appropriate solvent is treated with difluorodibromomethane until the reaction is complete. The obtained 1-(bromodifluoro methoxy)-3-(trifluoromethoxy)benzene is used with or without purification in the following reaction.

(b) 2,4-bis(trifluoromethoxy)benzene

A solution of 1-(bromodifluoromethoxy)-3-(trifluoro methoxy)benzene and a suitable base in an appropriate solvent is treated with hydrogen fluoride-pyridine complex or equivalent fluoride source until the reaction is complete. The obtained 1,3-bis(trifluoromethoxy)benzene is used with or without purification in the following reaction.

(c) 2,4-bis(trifluoromethoxy)phenylboronic acid

A solution of 1,3-bis(trifluoromethoxy)benzene in a non-protic solvent is treated at reduced temperature with a strong base such as sec-butyl lithium or the like. After sufficient time has elapsed to effect the lithiation of the ortho position, the reaction is quenched with trimethyl borate. After an appropriate workup procedure the crude 2,4-bis-(trifluoromethoxy)phenylboronic acid is used with or without purification in the following reaction.

(d) 2,4-bis(trifluoromethoxy)phenol

A solution of 2,4-bis(trifluoromethoxy)phenylboronic acid in a non-protic solvent is treated with hydrogen peroxide or an oxidative equivalent to generate 2,4-bis-(trifluoromethoxy)phenol after an appropriate workup.

Example 17

Preparation of 1-[3-(2,4-bis(trifluoromethoxy)phenoxy) propyloxy]-5-isopropyl biguanide, a compound of the formula I 2,4-bis(Trifluoromethoxy) phenol (example 16d) is converted to 1-[3-(2,4-bis(trifluoromethoxy)phenoxy) propyloxy]-5-isopropyl biguanide in substantially the same manner as previously described for the preparation of 1-[3-(2-chloro-4-trifluoromethoxyphenoxy) propyloxy]-5-isopropyl biguanide from 2-chloro-4-trifluoromethoxyphenol (Examples 10-14).

Example 18

Preparation of 4-chloro-3-trifluoromethoxyphenol, a compound of the formula VI

A solution of 3-trifluoromethoxyphenol and sulfuryl chloride is stirred at room temperature until conversion of starting material to product is complete. The excess of sulfuryl chloride is evaporated using a rotary evaporator. The residue is dissolved in dichloromethane and washed with water. The organic layer is separated, dried over $MgSO_4$, filtered and concentrated to yield crude 4-chloro-3-trifluoromethoxyphenol. The crude product is purified over a silica gel column using to give purified product that is used with or without further purification in the following reaction.

Example 19

Preparation of 1-[3-(4-chloro-3-trifluoromethoxy phenoxy)propyloxy]-5-isopropyl biguanide, a compound of the formula I 4-Chloro-3-trifluoromethoxyphenol is converted to 1-[3-(4-chloro-3-trifluoromethoxy phenoxy)propyloxy]-5-isopropyl biguanide in substantially the same manner as previously described for the preparation of 1-[3-(2-chloro-4-trifluoromethoxyphenoxy) propyloxy]-5-isopropyl biguanide from 2-chloro-4-trifluoromethoxyphenol (Examples 10-14).

Example 20

Preparation of 4,5-dichloro-2-trifluoromethoxyphenol, a compound of the formula VI (a) 1-acetoxy-3,4-dichlorophenol A solution of 3,4-dichlorophenol (Alfa Aesar, Ward Hill, Mass.) is treated with acetic anhydride and an appropriate base such as pyridine. When the reaction is complete the reaction mixture is diluted with aqueous hydrochloric acid and extracted with an organic solvent. The organic solvent is washed with water, dried over magnesium sulfate, filtered and rotary evaporated to give crude 1-acetoxy-3,4-dichlorobenzene that may be used with or without further purification in the following reaction.

(b) 2-acetyl-4,5-dichlorophenol

A solution of 1-acetoxy-3,4-dichlorobenzene in a solvent such as toluene is treated with $AlCl_3$ and heated until the reaction is complete. Following a suitable workup, the obtained crude 2-acetyl-4,5-dichlorophenol is used with or without further purification in the following reaction.

(c) 1-bromodifluoromethyl-2-acetyl-4,5-dichlorophenol

1-Bromodifluoromethoxy-2-acetyl-4,5-dichlorobenzene is prepared from 2-acetyl-4,5-dichlorophenol in a similar manner to that previously described for the preparation of 1-(bromodifluoromethoxy)-3-(trifluoromethoxy)benzene from 3-trifluoromethoxyphenol.

(d) 1-trifluoromethoxy-2-acetyl-4,5-dichlorobenzene

1-Trifluoromethoxy-2-acetyl-4,5-dichlorobenzene is prepared from 1-bromodifluoromethoxy-2-acetyl-4,5-dichlorobenzene in a similar manner to that previously described for the preparation of 1,3-bis(trifluoromethoxy)benzene from 1-(bromodifluoromethoxy)-3-(trifluoromethoxy)benzene.

(e) 4,5-dichloro-2-trifluoromethoxyphenol

A solution of 1-trifluoromethoxy-2-acetyl-4,5-dichlorobenzene is treated with meta-chloroperbenzoic acid in a solvent such as 1,2-dichlorethane. The solvent is removed and the residue is treated with aqueous base such as sodium hydroxide to give, after appropriate workup, the crude 4,5-dichloro-2-trifluoromethoxy phenol that can be used with or without further purification.

Example 21

Preparation of 1-[3-(4,5-dichloro-2-trifluoromethoxy phenoxy)propyloxy]-5-isopropyl biguanide, a compound of the formula I 4,5-Dichloro-2-trifluoromethoxyphenol is converted to 1-[3-(4,5-dichloro-2-trifluoromethoxy phenoxy)propyloxy]-5-isopropyl biguanide in substantially the same manner as that previously described for the preparation of 1-[3-(2-chloro-4-trifluoromethoxyphenoxy) propyloxy]-5-isopropyl biguanide from 2-chloro-4-trifluoromethoxyphenol (Examples 10-14).

Example 22

Preparation of 1-[3-(4-(trifluoromethanethio)phenoxy)propyloxy]-5-isopropyl biguanide, a compound of the formula I 4-(Trifluoromethanethio)phenol (Alfa Aesar, Ward Hill, Mass.) is converted to 1-[3-(4-(trifluoromethanethio)phenoxy)propyloxy]-5-isopropyl biguanide in substantially the same manner as that described for 1-[3-(4-trifluoromethoxy phenoxy)propyloxy]-5-isopropyl biguanide starting from 4-trifluoromethoxyphenol (Examples 1 to 4).

Example 23

Preparation of 1-[3-(4-(trifluoromethanesulfonamido)phenoxy)propyloxy]-5-isopropyl biguanide, a compound of the formula I 4-(Trifluoromethanesulfonamido)phenol (prepared as in Bergeron, Raymond, and Hoffman, Patrick, *J. Org. Chem.* 44(11), 1835-39 (1979)) is converted to 1-[3-(4-(trifluoromethanesulfonamido)-phenoxy) propyloxy]-5-isopropyl biguanide in substantially the same manner as that described for 1-[3-(4-trifluoromethoxy phenoxy)-propyloxy]-5-isopropyl biguanide starting from 4-trifluoromethoxyphenol (Examples 1-4).

Example 24

Preparation of 1-[3-(4-(trifluoromethanesulfonyl) phenoxy)propyloxy]-5-isopropyl biguanide, a compound of the formula I 4-(Trifluoromethanesulfonyl)phenol (as prepared in Lee, et al. U.S. Pat. No. 5,538,812) is converted to 1-[3-(4-(trifluoromethanesulfonyl)phenoxy) propyloxy]-5-isopropyl biguanide in substantially the same manner as that described for 1-[3-(4-trifluoromethoxy phenoxy)propyloxy]-5-isopropyl biguanide starting from 4-trifluoromethoxyphenol (Examples 1 to 4).

Example 25

Preparation of 1-[3-[(2,2,3,3-tetrafluorobenzodioxen-6-yl)oxy]propyloxy]-5-isopropyl biguanide, a compound of the formula I 2,2,3,3-Tetrafluoro-6-hydroxybenzodioxene ([CAS 103467-50-1] Oakwood 7950, Oakwood Products, Inc., West Columbia, S.C.) is converted to 1-[3-[(2,2,3,3-tetrafluorobenzodioxen-6-yl)oxy]propyloxy]-5-isopropyl biguanide in substantially the same manner as that described for 1-[3-(4-trifluoromethoxy phenoxy)propyloxy]-5-isopropyl biguanide starting from 4-trifluoromethoxyphenol (Examples 1 to 4).

Example 26

Preparation of 1-[3-(8-chloro-2,2,3,3-tetrafluorobenzodioxan-5-yl)oxy]propyloxy]-5-isopropyl biguanide, a compound of the formula I Step a: Preparation of 2,2,3,3-Tetrafluoro-5-hydroxybenzodioxene 2,2,3,3-Tetrafluoro-5-aminobenzodioxene ([CAS 119895-70-4] Oakwood 7818, Oakwood Products, Inc., West Columbia, S.C.) is dissolved in a solution of water and sulfuric acid and cooled. The cooled solution is treated portionwise with an aqueous solution of sodium nitrite and the obtained diazonium salt converted to 2,2,3,3-tetrafluoro-5-hydroxybenzodioxene under reflux and, if necessary, with catalysis.

Step b: Preparation of 1-[3-(8-Chloro-2,2,3,3-tetrafluorobenzodioxan-5-yl)oxy]propyloxy]-5-isopropyl biguanide 2,2,3,3-Tetrafluoro-5-hydroxybenzodioxene (from step a, above) is converted to 1-[3-(8-chloro-2,2,3,3-tetrafluorobenzodioxan-5-yl)oxy]propyloxy]-5-isopropyl biguanide in substantially the same manner as that described for 1-[3-(2-chloro-4-trifluoromethoxy phenoxy) propyloxy]-5-isopropyl-biguanide starting from 4-trifluoromethoxyphenol (Examples 9-14).

Example 27

Preparation of 1-[3-[7-chloro-2,2-difluorobenzodioxol-4-yloxy]propyloxy]-5-isopropyl biguanide, a compound of the formula I Step a: Preparation of 2,2-difluoro-4-hydroxybenzodioxole 2,2-Difluoro-4-aminobenzodioxole ([106876-54-4] Oakwood 7813, Oakwood Products, Inc., West Columbia, S.C.) is converted to 2,2-difluoro-4-hydroxybenzodioxole in substantially the same manner as that described for 2,2,3,3-tetrafluoro-5-hydroxybenzodioxene starting from 2,2,3,3-tetrafluoro-5-aminobenzodioxene (Example 26 step a).

Step b: Preparation of 1-[3-[(7-chloro-2,2-difluorobenzo-dioxol-4-yl)oxy]propyloxy]-5-isopropyl biguanide 2,2-Difluoro-4-hydroxybenzodioxole (from step a, above) is converted to 1-[3-[(7-chloro-2,2-difluorobenzodioxol-4-yl)oxy]propyloxy]-5-isopropyl biguanide in substantially the same manner as that described for 1-[3-(2-chloro-4-trifluoromethoxyphenoxy) propyloxy]-5-isopropyl-biguanide starting from 4-trifluoromethoxyphenol (Examples 9-14).

Example 28

Preparation of 1-[3-[2,2-difluorobenzodioxol-5-yloxy]propyloxy]-5-isopropyl biguanide, a compound of the formula I Step a: Preparation of 2,2-difluoro-5-hydroxybenzodioxole 2,2-Difluoro-5-aminobenzodioxole ([1544-85-0] Oakwood 7844, Oakwood Products, Inc., West Columbia, S.C.) is converted to 2,2-difluoro-5-hydroxybenzodioxole in substantially the same manner as that described for 2,2,3,3-tetrafluoro-5-hydroxy benzodioxene starting from 2,2,3,3-tetrafluoro-5-aminobenzodioxene (Example 26 step a).

Step b: Preparation of 1-[3-[2,2-difluorobenzodioxol-5-yloxy]propyloxy]-5-isopropyl biguanide 2,2-difluoro-5-hydroxybenzodioxole (from step a, above) is converted to 1-[3-[2,2-difluorobenzodioxol-5-yloxy]propyloxy]-5-isopropyl biguanide in substantially the same manner as that described for 1-[3-(4-trifluoromethoxy phenoxy)propyloxy]-5-isopropyl biguanide starting from 4-trifluoromethoxyphenol (Examples 1 to 4).

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A compound of formula I or a pharmaceutically acceptable salt thereof:

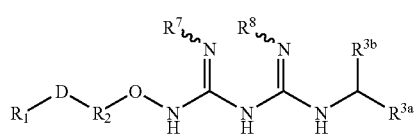

wherein:

$R^1$ is $R^x$, substituted aryl, substituted alkyl, substituted fused cycloalkylaryl, substituted aralkyl, substituted cycloalkylarylalkyl, substituted heteroaryl, or substituted heteroarylalkyl, wherein the latter seven groups are substituted with at least one substituent selected from the group consisting of —CN, —OCF$_3$, haloalkoxy, —SR$^4$, —OCF$_3$, —SCF$_3$, haloalkylthio, —NR$^5$R$^6$, —SO$_2$R$^4$, —SO$_2$NR$^5$R$^{6a}$, heteroaryl, heterocyclyl or $R^{10}$O—(CH$_2$CH$_2$O)$_j$—, or combinations thereof;

$R^x$ is substituted or unsubstituted:

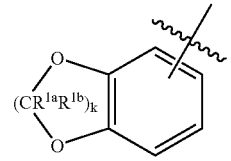

wherein each $R^{1a}$ and $R^{1b}$ are independently H, alkyl or fluoro;

$R^2$ is branched or straight chain lower alkylidene, or lower alkylene;

$R^{3a}$ and $R^{3b}$ are each independently hydrogen, lower alkyl, lower alkenyl, lower alkynyl, or taken together form a cycloalkyl group;

each $R^4$ is independently hydrogen, lower alkyl, substituted lower alkyl, lower alkenyl, substituted lower alkenyl, lower alkynyl, substituted lower alkynyl, aryl, substituted aryl, haloaryl, acyl, or heterocyclyl;

each $R^5$ is independently hydrogen, alkyl, substituted lower alkyl, lower alkenyl, substituted lower alkenyl, lower alkynyl, substituted lower alkynyl, alkyl substituted aryl, or acyl;

each $R^6$ is independently hydrogen, alkyl, substituted lower alkyl, lower alkenyl, substituted lower alkenyl, lower alkynyl, substituted lower alkynyl, alkyl substituted aryl, acyl, —SO$_2$R$^5$, or SO$_2$NR$^5$R$^5$; or $R^5$ and $R^6$ taken together with the atom to which they are attached form a heterocycle;

each $R^{6a}$ is independently hydrogen, alkyl, substituted lower alkyl, lower alkenyl, substituted lower alkenyl, lower alkynyl, substituted lower alkynyl, alkyl substituted aryl, acyl; or $R^5$ and $R^{6a}$ taken together with the atom to which they are attached form a heterocycle;

$R^7$ and $R^8$ are each, independently, hydrogen, alkyl, or acyl;

D is lower alkylidene, lower alkylene, —O—, —S—, or —N(R$^9$)—;

$R^9$ is hydrogen, alkyl, substituted lower alkyl, lower alkenyl, substituted lower alkenyl, lower alkynyl, substituted lower alkynyl, alkyl-substituted aryl, or acyl;

$R^{10}$ is alkyl or haloalkyl;

j is an integer from 1 to 20; and k is an integer from 1 to 4.

2. The compound of claim 1, wherein $R^1$ is substituted with at least one substituent selected from the group consisting of —OCF$_3$, haloalkoxy, —SCF$_3$, haloalkylthio or $R^{10}$O—(CH$_2$CH$_2$O)$_j$—.

3. The compound of claim 1, wherein $R^1$ is $R^x$, and $R^x$ is substituted or unsubstituted.

4. The compound of claim 3, wherein $R^x$ is substituted with one to four substituents selected, independently, from the group consisting of halo, —NO$_2$, —CN, —CF$_3$, —OCF$_3$, haloalkoxy, —SCF$_3$, haloalkylthio, haloalkyl, lower alkyl, spiroalkyl, aryl, alkoxy, —SR$^4$, —NR$^5$R$^6$, —SO$_2$R$^4$, —SO$^2$NR$^5$R$^{6a}$, heteroaryl, and heterocyclyl, and combinations thereof.

5. The compound of claim 1,
wherein when $R^1$ is substituted aryl, substituted alkyl, substituted fused cycloalkylaryl, substituted aralkyl, substituted cycloalkylarylalkyl, substituted heteroaryl, or substituted heteroarylalkyl, it is further substituted with one to four substituents selected, independently, from the group consisting of halo, $—NO_2$, $—CF_3$, haloalkyl, lower alkyl, spiroalkyl, aryl, and alkoxy, and combinations thereof.

6. The compound of claim 1,
wherein $R^1$ is substituted with at least one $—SR^4$.

7. The compound of claim 1,
wherein:
$R^1$ is 4-(trifluoromethanethio)-phenyl;
D is —O—; and
$R^7$ and $R^8$ are each hydrogen.

8. The compound of claim 1,
wherein $R^1$ is substituted with at least one $—NR^5R^6$.

9. The compound of claim 1,
wherein:
$R^1$ is 4-(trifluoromethanesulfonamido)-phenyl;
D is —O—; and
$R^7$ and $R^8$ are each hydrogen.

10. The compound of claim 1,
wherein $R^1$ is substituted with at least one $—SO_2R^4$.

11. The compound of claim 1,
wherein:
$R^1$ is 4-(trifluoromethanesulfonyl)phenyl;
D is —O—; and
$R^7$ and $R^8$ are each hydrogen.

12. The compound of claim 1,
wherein:
$R^1$ is 2,4-bis-trifluoromethoxyphenyl;
D is —O—; and
$R^7$ and $R^8$ are each hydrogen.

13. The compound of claim 1,
wherein:
$R^1$ is 4-chloro-3- trifluoromethoxyphenyl;
D is —O—; and
$R^7$ and $R^8$ are each hydrogen.

14. The compound of claim 1,
wherein:
$R^1$ is 4,5-dichloro-2-trifluoromethoxyphenyl,
D is —O—; and
$R^7$ and $R^8$ are each hydrogen.

15. The compound of claim 1,
wherein:
$R^1$ is 2-chloro-4-trifluoromethoxyphenyl;
D is —O—; and
$R^7$ and $R^8$ are each hydrogen.

16. The compound of claim 1,
wherein:
$R^1$ is 4-chloro-2-trifluoromethoxyphenyl;
D is —O—; and
$R^7$ and $R^8$ are each hydrogen.

17. The compound of claim 1,
wherein $R^{3a}$ and $R^{3b}$ are methyl, or taken together form a cyclopropyl group.

18. The compound of claim 1,
wherein $R^1$ is substituted with —CN or $—OCF_3$.

19. The compound of claim 1,
wherein $R^1$ is substituted with $—SCF_3$, $—SO_2CF_3$, or $—NHSO_2CF_3$.

20. The compound of claim 1,
wherein said compound is:
1-(3-(4-trifluoromethoxyphenoxy)propyloxy)-5-isopropyl biguanide;
1-(3-(4-trifluoromethoxyphenoxy)propyloxy)-5-isopropyl biguanide hemisuccinate;
1-(3-(4-trifluoromethoxyphenoxy)propyloxy)-5-cyclopropyl biguanide;
1-(3-(4-trifluoromethoxyphenoxy)propyloxy)-5-cyclopropyl biguanide hydrochloride;
1-[3-(2-chloro-4-trifluoromethoxyphenoxy)propyloxy]-5-isopropyl biguanide;
1-[3-(2-chloro-4-trifluoromethoxyphenoxy)propyloxy]-5-isopropyl biguanide phosphate salt;
1-[3-(4-chloro-2-trifluoromethoxyphenoxy)propyloxy]-5-isopropyl biguanide;
1-[3-(4-chloro-2-trifluoromethoxyphenoxy)propyloxy]-5-isopropyl biguanide, mono phosphate salt;
1-[3-(4-chloro-2-trifluoromethoxyphenoxy)propyloxy]-5-isopropyl biguanide, bis phosphate salt;
1-[3-(2,4-bis(trifluoromethoxy)phenoxy)propyloxy]-5-isopropyl biguanide;
1-[3-(4-chloro-3-trifluoromethoxy phenoxy)propyloxy]-5-isopropyl biguanide;
1-[3-(4,5-dichloro-2-trifluoromethoxy phenoxy)propyloxy]-5-isopropyl biguanide;
1-[3-(2,2,3,3-Tetrafluoro-2,3-dihydro-benzo[1,4]dioxin-6-yloxy)propyloxy]-5-isopropyl biguanide;
1-[3-(2,2-Difluoro-benzo[1,3]dioxol-5-yloxy)propyloxy]-5-isopropyl biguanide;
1-[3-(4-(trifluoromethanethio)phenoxy)propyloxyl-5-isopropyl biguanide;
1-[3-(4-(trifluoromethanesulfonamido)phenoxy) propyloxy]-5-isopropyl biguanide; or
1-[3-(4-(trifluoromethanesulfonyl)phenoxy)propyloxy]-5-isopropyl biguanide.

21. A compound of claim 1, wherein when $R^x$ is:

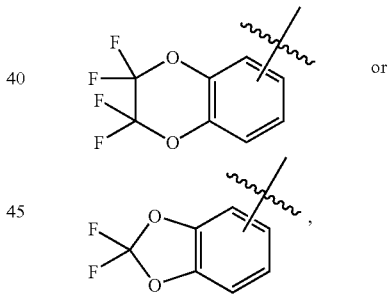

optionally substituted.

22. The compound of claim 5,
wherein $R^1$ is substituted aryl, substituted cycloalkylaryl, substituted aralkyl, or substituted cycloalkylarylalkyl.

23. The compound of claim 6,
wherein $R^4$ of said $—SR^4$ is substituted lower alkyl.

24. The compound of claim 8,
wherein $R^6$ is $—SO_2R^5$ or $—SO_2NR^5R^{6a}$.

25. The compound of claim 10,
wherein $R^4$ of said $—SO_2R^4$ is substituted lower alkyl.

26. The compound of claim 20, wherein said compound is:
1-(3-(4-trifluoromethoxyphenoxy)propyloxy)-5-isopropyl biguanide;
1-(3-(4-trifluoromethoxyphenoxy)propyloxy)-5-isopropyl biguanide hemisuccinate;

1-(3-(4-trifluoromethoxyphenoxy)propyloxy)-5-cyclopropyl biguanide;
1-(3-(4-trifluoromethoxyphenoxy)propyloxy)-5-cyclopropyl biguanide hydrochloride;
1-[3-(2-chloro-4-trifluoromethoxyphenoxy)propyloxy]-5-isopropyl biguanide;
1-[3-(2-chloro-4-trifluoromethoxyphenoxy)propyloxy]-5-isopropyl biguanide phosphate salt;
1-[3-(4-chloro-2-trifluoromethoxyphenoxy)propyloxy]-5-isopropyl biguanide;
1-[3-(4-chloro-2-trifluoromethoxyphenoxy)propyloxy]-5-isopropyl biguanide, mono phosphate salt; or
1-[3-(4-chloro-2-trifluoromethoxyphenoxy)propyloxy]-5-isopropyl biguanide, bis phosphate salt.

27. The compound of claim 21, wherein:
D is —O—; and
$R^7$ and $R^8$ are each hydrogen.

28. The compound of claim 22,
wherein $R^1$ is mono- or polysubstituted phenyl; and
wherein $R^{3a}$ and $R^{3b}$ are each independently lower alkyl, or taken together form a cycloalkyl group.

29. The compound of claim 23,
wherein said lower alkyl of $R^4$ is substituted with at least one halo.

30. The compound of claim 24,
wherein $R^6$ is —$SO_2R^5$.

31. The compound of claim 25,
wherein said lower alkyl of said $R^4$ is substituted with at least one halo.

32. The compound of claim 27, wherein:
$R^{3a}$ and $R^{3b}$ are each methyl, or taken together form a cyclopropyl.

33. The compound of claim 28,
wherein:
$R^1$ is monosubstituted phenyl.

34. The compound of claim 28,
wherein said phenyl is substituted with at least one —$OCF_3$.

35. The compound of claim 29,
wherein said halo of $R^4$ is —F.

36. The compound of claim 30,
wherein $R^5$ of said —$SO_2R^5$ is substituted lower alkyl.

37. The compound of claim 31,
wherein said halo of $R^4$ is —F.

38. The compound of claim 32, wherein:
$R^2$ is —$CH_2CH_2CH_2$—.

39. The compound of claim 33,
wherein:
$R^1$ is phenyl substituted with —$OCF_3$.

40. The compound of claim 34,
wherein said phenyl is substituted with at least two —$OCF_3$.

41. The compound of claim 34,
wherein said phenyl, substituted with at least one —$OCF_3$, is further substituted with at least one halo.

42. The compound of claim 34,
wherein said $R^{3a}$ and said $R^{3b}$ are each methyl.

43. The compound of claim 35,
wherein $R^4$ is —$CF_3$.

44. The compound of claim 36,
wherein said lower alkyl of $R^5$ is substituted with at least one halo.

45. The compound of claim 37,
wherein said alkyl of said $R^4$ is —$CF_3$.

46. The compound of claim 38, wherein $R^1$, optionally substituted, is:

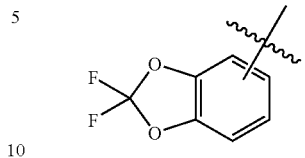

47. The compound of claim 38, wherein $R^1$, optionally substituted, is:

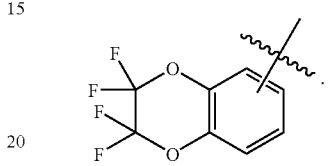

48. The compound of claim 39,
wherein:
$R^{3a}$ and $R^{3b}$ are each methyl, or taken together form a cyclopropyl.

49. The compound of claim 40,
wherein said phenyl is substituted with two —$OCF_3$.

50. The compound of claim 40,
wherein said $R^{3a}$ and said $R^{3b}$ are each methyl, or taken together form a cyclopropyl.

51. The compound of claim 40,
wherein said halo of said substituted phenyl is —Cl.

52. The compound of claim 41,
wherein said $R^{3a}$ and said $R^{3b}$ are each methyl, or taken together form a cyclopropyl.

53. The compound of claim 42,
wherein $R^2$ is —$CH_2CH_2CH_2$—.

54. The compound of claim 43,
wherein $R^{3a}$ and $R^{3b}$ are each methyl, or taken together form a cyclopropyl.

55. The compound of claim 44,
wherein said halo of $R^5$ is —F.

56. The compound of claim 45,
wherein $R^{3a}$ and $R^{3b}$ are each methyl, or taken together form a cyclopropyl.

57. The compound of claim 46, wherein $R^{3a}$ and $R^{3b}$ are each methyl.

58. The compound of claim 47, wherein $R^{3a}$ and $R^{3b}$ are each methyl.

59. The compound of claim 48,
wherein:
$R^1$ is para-trifluoromethoxyphenyl; and
D is —O—.

60. The compound of claim 52,
wherein said $R^{3a}$ and said $R^{3b}$ are each methyl.

61. The compound of claim 53,
wherein:
$R^1$ is 2,4-bis-trifluoromethoxyphenyl;
D is —O—; and
$R^7$ and $R^8$ are each hydrogen.

62. The compound of claim 53,
wherein:
$R^1$ is 4-chloro-3- trifluoromethoxyphenyl;
D is —O—; and
$R^7$ and $R^8$ are each hydrogen.

63. The compound of claim 53,
wherein:
$R^1$ is 4,5-dichloro-2-trifluoromethoxyphenyl;
D is —O—; and
$R^7$ and $R^8$ are each hydrogen.

64. The compound of claim 53,
wherein:
$R^1$ is 2-chloro-4-trifluoromethoxyphenyl;
D is —O—; and
$R^7$ and $R^8$ are each hydrogen.

65. The compound of claim 53,
wherein:
$R^1$ is 4-chloro-2-trifluoromethoxyphenyl;
D is —O—; and
$R^7$ and $R^8$ are each hydrogen.

66. The compound of claim 54,
wherein $R^{3a}$ and $R^{3b}$ are each methyl.

67. The compound of claim 55,
wherein said alkyl of $R^5$ is —CF$_3$.

68. The compound of claim 56,
wherein $R^{3a}$ and $R^{3b}$ are each methyl.

69. The compound of claim 57, wherein $R^1$ is:

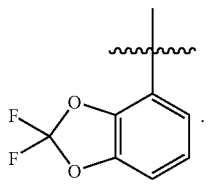

70. The compound of claim 57, wherein $R^1$ is:

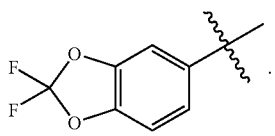

71. The compound of claim 58, wherein $R^1$ is:

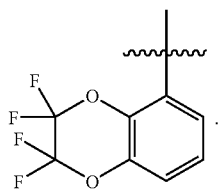

72. The compound of claim 58, wherein $R^1$ is:

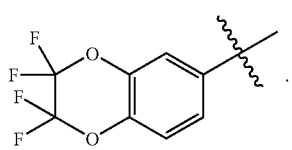

73. The compound of claim 59,
wherein:
$R^7$ and $R^8$ are each hydrogen.

74. The compound of claim 60,
wherein said $R^2$ is —CH$_2$CH$_2$CH$_2$—.

75. The compound of claim 66,
wherein $R^2$ is —CH$_2$CH$_2$CH$_2$—.

76. The compound of claim 67,
wherein $R^{3a}$ and $R^{3b}$ are each methyl, or taken together form a cyclopropyl.

77. The compound of claim 68,
wherein $R^2$ is —CH$_2$CH$_2$CH$_2$—.

78. The compound of claim 73,
wherein $R^2$ is —CH$_2$CH$_2$CH$_2$—.

79. The compound of claim 75,
wherein:
$R^1$ is 4-(trifluoromethanethio)-phenyl;
D is —O—; and
$R^7$ and $R^8$ are each hydrogen.

80. The compound of claim 76,
wherein:
$R^1$ is 4-(trifluoromethanesulfonyl)phenyl;
D is —O—; and
$R^7$ and $R^8$ are each hydrogen.

81. The compound of claim 77,
wherein $R^{3a}$ and $R^{3b}$ are each methyl.

82. The compound of claim 78,
wherein $R^{3a}$ and $R^{3b}$ are each methyl.

83. The compound of claim 78,
wherein $R^{3a}$ and $R^{3b}$ taken together form a cyclopropyl.

84. The compound of claim 80,
wherein $R^2$ is —CH$_2$CH$_2$CH$_2$—.

85. The compound of claim 84,
wherein:
$R^1$ is 4-(trifluoromethanesulfonamido)-phenyl;
D is —O—; and
$R^7$ and $R^8$ are each hydrogen.

86. A composition, comprising:
at least one compound according to claim 1; and
at least one pharmaceutically acceptable carrier.

87. The composition of claim 86, further comprising at least one or more anti-malarial agent or anti-infective agent.

88. The composition of claim 86, further comprising at least one sulfonamide or sulfone.

89. A process for preparing antimicrobial compounds, comprising the steps of:
contacting a compound of formula II:

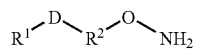

with a compound of formula III:

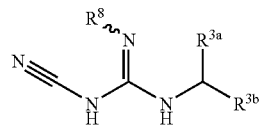

to provide a compound of formula I:

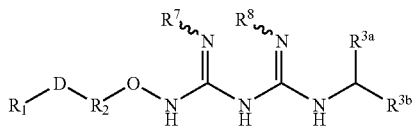

wherein:
- $R^1$ is $R^x$, substituted aryl, substituted alkyl, substituted fused cycloalkylaryl, substituted aralkyl, substituted cycloalkylarylalkyl, substituted heteroaryl, or substituted heteroarylalkyl, wherein the latter seven groups are substituted with at least one substituent selected from the group consisting of —CN, —OCF$_3$, haloalkoxy, —SR$^4$, —OCF$_3$, —SCF$_3$, haloalkylthio, —NR$^5$R$^6$, —SO$_2$R$^4$, —SO$_2$NR$^5$R$^{6a}$, heteroaryl, heterocyclyl or $R^{10}$O—(CH$_2$CH$_2$O)$_j$—, or combinations thereof;
- $R^x$ is substituted or unsubstituted:

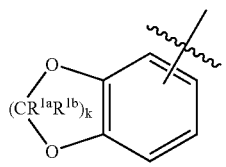

wherein each $R^{1a}$ and $R^{1b}$ bare independently H, alkyl or fluoro;
- $R^2$ is branched or straight chain lower alkylidene, or lower alkylene;
- $R^{3a}$ and $R^{3b}$ are each independently hydrogen, lower alkyl, lower alkenyl, lower alkynyl, or taken together form a cycloalkyl or spiroalkyl group;
- each $R^4$ is independently hydrogen, lower alkyl, substituted lower alkyl, lower alkenyl, substituted lower alkenyl, lower alkynyl, substituted lower alkynyl, aryl, substituted aryl, haloaryl, acyl, or heterocyclyl;
- each $R^5$ is independently hydrogen, alkyl, substituted lower alkyl, lower alkenyl, substituted lower alkenyl, lower alkynyl, substituted lower alkynyl, alkyl substituted aryl, or acyl;
- each $R^6$ is independently hydrogen, alkyl, substituted lower alkyl, lower alkenyl, substituted lower alkenyl, lower alkynyl, substituted lower alkynyl, alkyl substituted aryl, acyl, —SO$_2$R$^5$, or SO$_2$NR$^5$R$^5$; or $R^5$ and $R^6$ taken together with the atom to which they are attached form a heterocycle;
- each $R^{6a}$ is independently hydrogen, alkyl, substituted lower alkyl, lower alkenyl, substituted lower alkenyl, lower alkynyl, substituted lower alkynyl, alkyl substituted aryl, acyl; or $R^5$ and $R^{6a}$ taken together with the atom to which they are attached form a heterocycle;
- $R^7$ and $R^8$ are each, independently, hydrogen, alkyl, or acyl;
- D is lower alkylidene, lower alkylene, —O—, —S—, or —N(R$^9$)—;
- $R^9$ is hydrogen, alkyl, substituted lower alkyl, lower alkenyl, substituted lower alkenyl, lower alkynyl, substituted lower alkynyl, alkyl-substituted aryl, or acyl;
- $R^{10}$ is alkyl or haloalkyl;
- j is an integer from 1 to 20; and
- k is an integer from 1 to 4;

or a pharmaceutically acceptable salt thereof.

90. A method for reducing in a patient the level of infection caused by an organism selected from the group consisting of *Plasmodium* sp., *Mycobacterium* sp., *Toxoplasma gondii*, and *Pneumocystis carinii*, comprising the step of:
administering to said patient in need thereof an effective amount of one or more compounds according to claim 1.

91. A method for protecting a patient susceptible to infection caused by exposure to *Plasmodium* sp. comprising the step of:
administering to said patient in need thereof an effective amount of one or more compounds according to claim 1.

* * * * *